United States Patent
Ohshima et al.

(10) Patent No.: US 9,611,279 B2
(45) Date of Patent: Apr. 4, 2017

(54) ZINC COMPLEX

(71) Applicant: TAKASAGO INTERNATIONAL CORPORATION, Tokyo (JP)

(72) Inventors: Takashi Ohshima, Fukuoka (JP); Ryo Yazaki, Fukuoka (JP); Yuki Yokote, Ichihara (JP); Yoshimasa Matsushima, Kamakura (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 47 days.

(21) Appl. No.: 14/769,147

(22) PCT Filed: Mar. 27, 2014

(86) PCT No.: PCT/JP2014/058876
§ 371 (c)(1),
(2) Date: Aug. 20, 2015

(87) PCT Pub. No.: WO2014/157524
PCT Pub. Date: Oct. 2, 2014

(65) Prior Publication Data
US 2016/0002268 A1  Jan. 7, 2016

(30) Foreign Application Priority Data
Mar. 27, 2013 (JP) ................. 2013-066741

(51) Int. Cl.
| | |
|---|---|
| C07F 3/06 | (2006.01) |
| C07D 233/61 | (2006.01) |
| C07C 53/18 | (2006.01) |
| B01J 31/16 | (2006.01) |
| B01J 31/18 | (2006.01) |
| B01J 31/22 | (2006.01) |
| C07B 41/12 | (2006.01) |
| C07C 29/128 | (2006.01) |

(52) U.S. Cl.
CPC ............ *C07F 3/06* (2013.01); *B01J 31/1691* (2013.01); *B01J 31/181* (2013.01); *B01J 31/182* (2013.01); *B01J 31/1815* (2013.01); *B01J 31/2208* (2013.01); *B01J 31/2226* (2013.01); *C07B 41/12* (2013.01); *C07C 29/1285* (2013.01); *C07C 53/18* (2013.01); *C07D 233/61* (2013.01); *B01J 2231/49* (2013.01); *B01J 2531/0205* (2013.01); *B01J 2531/0216* (2013.01); *B01J 2531/26* (2013.01)

(58) Field of Classification Search
CPC ...................................................... C07F 3/06
See application file for complete search history.

(56) References Cited

U.S. PATENT DOCUMENTS
2009/0198070 A1  8/2009  Mashima et al.
2010/0249422 A1  9/2010  Mashima et al.
2011/0098479 A1  4/2011  Mashima et al.
2012/0172601 A1  7/2012  Matsushima et al.
2013/0190502 A1  7/2013  Mashima et al.

FOREIGN PATENT DOCUMENTS
| | | |
|---|---|---|
| JP | 2007-099730 A | 4/2007 |
| JP | 2009-185033 A | 8/2009 |
| JP | 2011-079810 A | 4/2011 |
| JP | 2014-019664 A | 2/2014 |
| WO | 2009/047905 A1 | 4/2009 |

OTHER PUBLICATIONS

Pellei et al. CAS Accession No. 2000:910763.*
Takanori Iwasaki et al., "Transesterification of Various Methyl Esters Under Mild Conditions Catalyzed by Tetranuclear Zinc Cluster," J. Org. Chem., 2008, pp. 5147-5150, vol. 73.
Takashi Ohshima et al., "Enzyme-Like Chemoselective Acylation of Alcohols in the Presence of Amines Catalyzed by a Tetranuclear Zinc Cluster," J. Am. Chem. Soc., 2008, pp. 2944-2945, vol. 130.
Takanori Iwasaki et al., "A Simple, General, and Highly Chemoselective Acetylation of Alcohols Using Ethyl Acetate as the Acetyl Donor Catalyzed by a Tetranuclear Zinc Cluster," SYNLETT, 2009, pp. 1659-1663, No. 10.
Takanori Iwasaki et al., "A Tetranuclear-Zinc-Cluster-Catalyzed Practical and Versatile Deprotection of Acetates and Benzoates," Chem. Eur. J., 2010, pp. 11567-11571, vol. 16.
Yusuke Maegawa et al., "Additive Effect of N-Heteroaromatics on Transesterification Catalyzed by Tetranuclear Zinc Cluster," ACS Catalysis, 2011, pp. 1178-1182, vol. 1.
Yan Ding et al., "Controllable assemby of four new POM-based supramolecular compounds by altering the POM secondary building units from pseudo-Keggin to classical Keggin," CrystEngComm, 2011, pp. 2687-2692, vol. 13.
Peng Du et al., "A series of MOFs based on a tricarboxylic acid and various N-donor ligands: syntheses, structures, and properties," CrystEngComm, 2013, pp. 6986-7002, vol. 15.

(Continued)

*Primary Examiner* — Joseph Kosack
(74) *Attorney, Agent, or Firm* — Sughrue Mion, PLLC

(57) ABSTRACT

A zinc complex characterized in exhibiting an octahedral structure and being configured from repeating units represented by general formula (I):

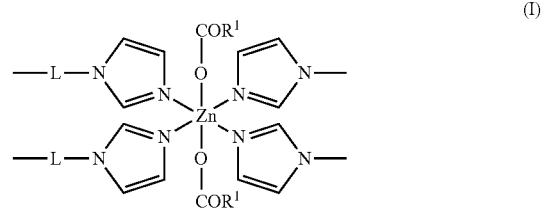

wherein L represents a linker region, and $R^1$ represents a C1-4 alkyl group, which can have a halogen atom.

16 Claims, 4 Drawing Sheets

(56) References Cited

OTHER PUBLICATIONS

Ying-Ying Liu et al., "Versatile frameworks constructed from divalent metals and 1,2,3,4-butanetetracarboxylate anion: syntheses, crystal structures, luminescence and magnetic properties," CrystEngComm, 2008, pp. 894-904, vol. 10.

Julie Brown et al., "Preparation, Characterization, and Thermal Properties of Controllable Metal-Imidazole Complex Curing Agents for Epoxy Resins," Journal of Applied Polymer Science, 2000, pp. 201-217, vol. 75.

International Searching Authority, International Search Report of PCT/JP2014/058876 dated May 13, 2014.

* cited by examiner

ZINC COMPLEX

CROSS REFERENCE TO RELATED APPLICATIONS

This is a National Stage of International Application No. PCT/JP2014/058876 filed Mar. 27, 2014, claiming priority based on Japanese Patent Application No. 2013-066741 filed Mar. 27, 2013, the contents of all of which are incorporated herein by reference in their entirety.

TECHNICAL FIELD

The present invention relates to a novel zinc complex useful as a catalyst for various reactions including transesterification reaction and the like.

BACKGROUND ART

A lot of multinuclear metal complexes having multiple metal nuclei in each molecule have been developed as highly active catalysts. Of these catalysts, a catalyst comprising a trifluoroacetate-bridged tetranuclear zinc cluster complex containing four zinc ions in a molecule is an excellent catalyst which promotes various reactions such as transesterification reaction, hydroxy group-selective acylation reaction in the presence of an amino group, acetylation reaction, deacetylation reaction, and amidation reaction in an environmentally friendly manner with less by-products (for example, Japanese Patent Application Publication No. 2009-185033, Domestic Re-publication of PCT International Publication No. 2009-047905, Japanese Patent Application Publication No. 2011-079810, J. Org. Chem. 2008, 73, 5147, J. Am. Chem. Soc. 2008, 130, 2944, Synlett 2009, 10, 1659, and Chem, Eur, J. 2010, 16, 11567).

The tetranuclear zinc cluster catalyst $Zn_4(OCOCF_3)_6O$ is an excellent catalyst, but it cannot be said that the activity of the catalyst is sufficient. As described in ACS Catal, 2011, 1, 1178, some reports say that the activity is improved to some degree by adding a nitrogen-containing aromatic compound such as DMAP (4-dimethylaminopyridine) or NMI (N-methylimidazole) to improve the activity; however, there still remains a problem of the need for an excess of the additive relative to the catalyst. Moreover, since the tetranuclear zinc cluster catalyst gradually decomposes and loses its activity with the progress of the reaction, the catalyst is difficult to recover and reuse.

SUMMARY OF INVENTION

An object of the present invention is to provide a novel zinc complex which is highly active as a catalyst, has stability, and further is easy to recover and reuse.

The present inventors have conducted intensive study, and consequently found that a zinc complex which achieves the above-described object can be obtained by mixing a zinc carboxylate compound with a bidentate ligand in which two imidazole groups are connected by a suitable linker.

The present invention relates to the following [1] to [10].

[1] A zinc complex with an octahedral geometry, comprising a repeating unit represented by the following general formula (I):

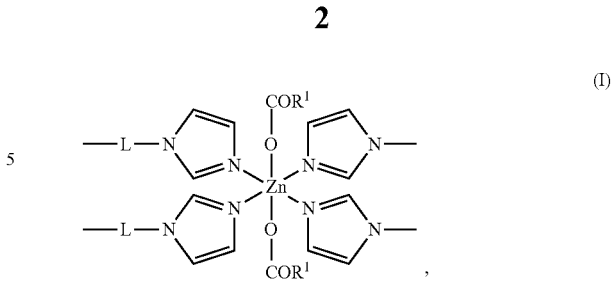

wherein L represents a linker moiety, and $R^1$ represents an alkyl group having 1 to 4 carbon atoms and optionally having a halogen atom(s).

[2] A zinc complex obtained by reacting
a zinc carboxylate compound represented by general formula (III) or a zinc carboxylate compound represented by general formula (IV) with
a compound represented by general formula (V) in an amount of 2 mole equivalents to zinc atoms of the zinc carboxylate compound:

$$Zn(OCOR^{1a})_2 \cdot xH_2O \quad (III),$$

wherein $R^{1a}$ represents an alkyl group having 1 to 4 carbon atoms and optionally having a halogen atom(s), and x represents any number of 0 or greater;

$$Zn_4O(OCOR^{1b})_6(R^{1b}COOH)_n \quad (IV),$$

wherein $R^{1b}$ represents an alkyl group having 1 to 4 carbon atoms and optionally having a halogen atom(s), and n represents 0 to 1; and

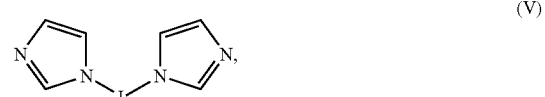

wherein L represents a linker moiety.

[3] The zinc complex according to the above-described [1] or [2], wherein
the linker L is represented by the following general formula (II):

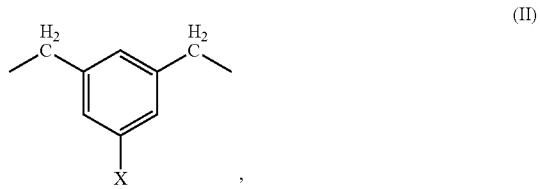

wherein X represents a hydrogen atom, an optionally substituted alkyl group having 1 to 10 carbon atoms, an optionally substituted alkoxy group having 1 to 10 carbon atoms, an optionally substituted aryl group, an optionally substituted allyl group, or a substituted amino group.

[4] A catalyst comprising the zinc complex according to any one of the above-described [1] to [3].

[5] A method for acylating a hydroxy group, comprising reacting a carboxylic acid or an ester thereof in the presence of the catalyst according to the above-described [4].

[6] A method for converting a hydroxy group to a carbonate, comprising
reacting a carbonate ester in the presence of the catalyst according to the above-described [4].

[7] A method for deacylating a carboxylate ester, comprising
deacylating the carboxylate ester in the presence of the catalyst according to the above-described [4].

[8] A method for acylating a hydroxy group with a carboxylic acid or an ester thereof, comprising
forming a catalyst by adding a zinc carboxylate compound represented by general formula (III) or a zinc carboxylate compound represented by general formula (IV) together with a compound represented by general formula (V) to an acylation reaction system:

$$Zn(OCOR^{1a})_2 \cdot xH_2O \qquad (III),$$

wherein $R^{1a}$ represents an alkyl group having 1 to 4 carbon atoms and optionally having a halogen atom(s), and x represents any number of 0 or greater;

$$Zn_4O(OCOR^{1b})_6(R^{1b}COOH)_n \qquad (IV),$$

wherein $R^{1b}$ represents an alkyl group having 1 to 4 carbon atoms and optionally having a halogen atom(s), and n represents 0 to 1; and

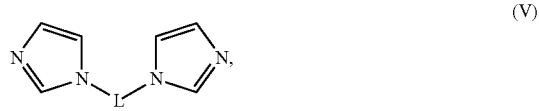
(V)

wherein L represents a linker moiety.

[9] A method for converting a hydroxy group to a carbonate with a carbonate ester, comprising
forming a catalyst by adding a zinc carboxylate compound represented by general formula (III) or a zinc carboxylate compound represented by general formula (IV) together with a compound represented by general formula (V) to a carbonate formation reaction system:

$$Zn(OCOR^{1a})_2 \cdot xH_2O \qquad (III),$$

wherein $R^{1a}$ represents an alkyl group having 1 to 4 carbon atoms and optionally having a halogen atom(s), and x represents any number of 0 or greater;

$$Zn_4O(OCOR^{1b})_6(R^{1b}COOH)_n \qquad (IV),$$

wherein $R^{1b}$ represents an alkyl group having 1 to 4 carbon atoms and optionally having a halogen atom(s), and n represents 0 to 1; and

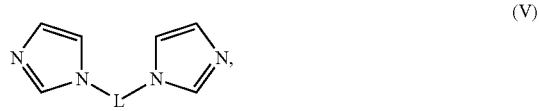
(V)

wherein L represents a linker moiety.

[10] A method for deacylating a carboxylate ester, comprising
forming a catalyst by adding a zinc carboxylate compound represented by general formula (III) or a zinc carboxylate compound represented by general formula (IV) together with a compound represented by general formula (V) to a deacylation reaction system:

$$Zn(OCOR^{1a})_2 \cdot xH_2O \qquad (III),$$

wherein $R^{1a}$ represents an alkyl group having 1 to 4 carbon atoms and optionally having a halogen atom(s), and x represents any number of 0 or greater;

$$Zn_4O(OCOR^{1b})_6(R^{1b}COOH)_n \qquad (IV),$$

wherein $R^{1b}$ represents an alkyl group having 1 to 4 carbon atoms and optionally having a halogen atom(s), and n represents 0 to 1; and

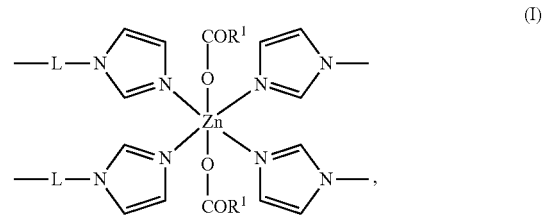
(V)

wherein L represents a linker moiety.

[11] A method for producing a zinc complex represented by general formula (I), comprising
reacting a zinc carboxylate compound represented by general formula (III) or a zinc carboxylate compound represented by general formula (IV) with
a compound represented by general formula (V) in an amount of 2 mole equivalents to zinc atoms of the zinc carboxylate compound:

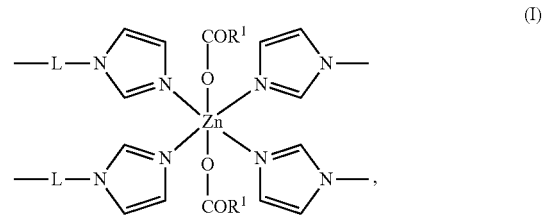
(I)

wherein L represents a linker moiety, and $R^1$ represents an alkyl group having 1 to 4 carbon atoms and optionally having a halogen atom(s);

$$Zn(OCOR^{1a})_2 \cdot xH_2O \qquad (III),$$

wherein $R^{1a}$ represents an alkyl group having 1 to 4 carbon atoms and optionally having a halogen atom(s), and x represents any number of 0 or greater;

$$Zn_4O(OCOR^{1b})_6(R^{1b}COOH)_n \qquad (IV),$$

wherein $R^{1b}$ represents an alkyl group having 1 to 4 carbon atoms and optionally having a halogen atom(s), and n represents 0 to 1; and

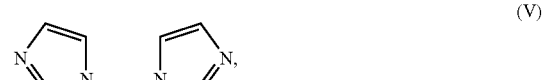
(V)

wherein L represents a linker moiety.

The zinc complex represented by general formula (I) of the present invention is highly active as a catalyst, has stability, and further is easy to recover and reuse. Hence, this zinc complex enables reactions with good environmental friendliness, good handleability, and further good economical efficiency. Moreover, the zinc complex of the present invention is useful as a catalyst for synthesis of intermediates for pharmaceutical and agricultural chemicals, functional materials, and structural materials, and the like.

DESCRIPTION OF EMBODIMENTS

Figure 1:
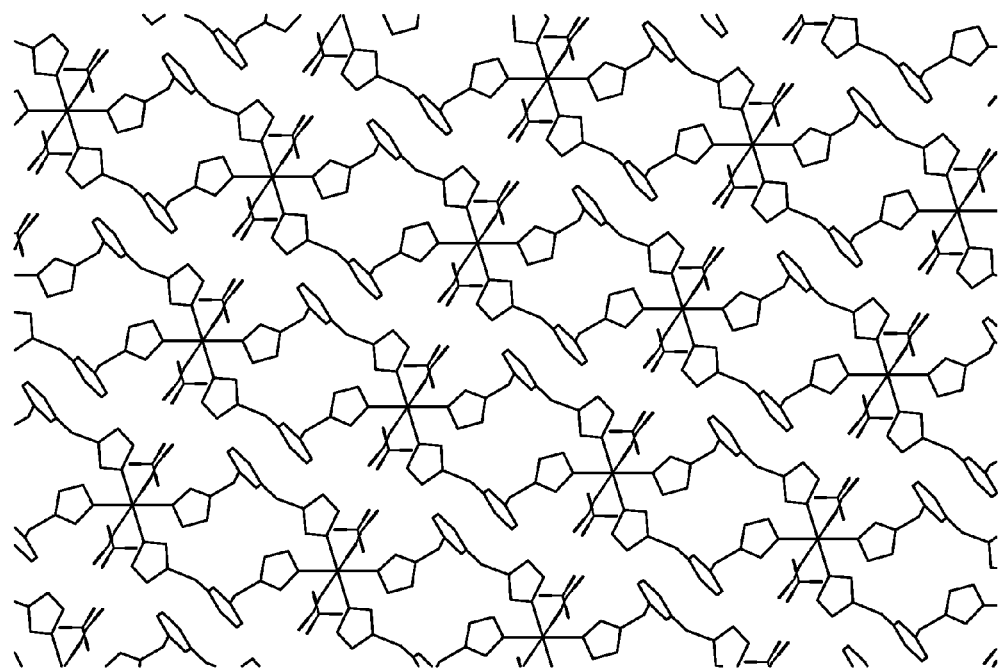
FIG. 1 shows a result of X-ray crystallography of a zinc complex A with an octahedral geometry of the present invention.
Figure 1:
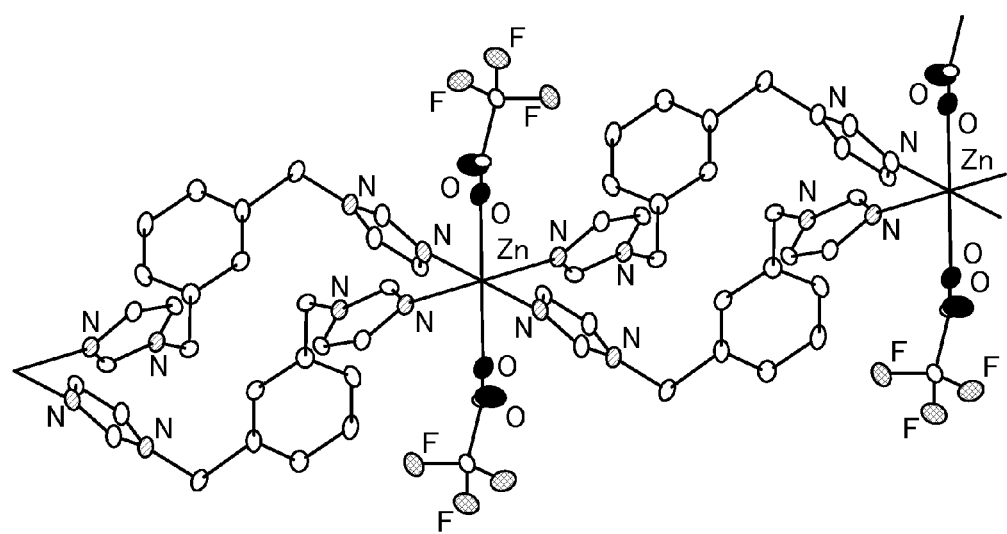

Hereinafter, the present invention will be described specifically.

A zinc complex of the present invention is a zinc complex with an octahedral geometry comprising a repeating unit represented by the following general formula (I):

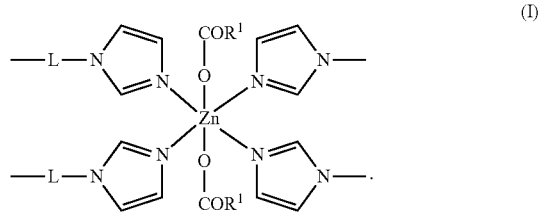

(I)

In general formula (I), L represents a linker moiety. L represents a divalent group of atoms which bridges nitrogen atoms on one side of two imidazole groups.

The divalent group of atoms may be linear or branched. The divalent group of atoms may be a linear or branched alkylene group having 1 to 20 carbon atoms, a cycloalkylene group having 3 to 8 carbon atoms, a linear or branched alkenylene group having 2 to 20 carbon atoms, a cycloalkenylene group having 3 to 20 carbon atoms, a linear or branched alkynylene group having 2 to 20 carbon atoms, an arylene group having 6 to 20 carbon atoms, an arylalkylene group having 8 to 20 carbon atoms, a heteroalkylene group having 1 to 20 carbon atoms, a heteroarylene group having 2 to 20 carbon atoms, a heteroarylalkylene group having 3 to 20 carbon atoms, a phenylenevinylene group, a polyfluorene diyl group, a polythiophene diyl group, a dialkylsilane diyl group, or a diarylsilane diyl group. These divalent groups of atoms optionally have substituents. Moreover, any two or more of these groups of atoms may be employed in combination.

Of these divalent groups of atoms, preferred are optionally substituted alkylene groups, optionally substituted arylene groups, optionally substituted heteroalkylene groups, optionally substituted arylalkylene groups, and optionally substituted heteroarylalkylene groups which may be linear or branched. More preferred are optionally substituted arylalkylene groups and optionally substituted heteroarylalkylene groups which may be linear or branched, and further preferred are optionally substituted arylalkylene groups which may be linear or branched.

Examples of the linear or branched alkylene group having 1 to 20 carbon atoms include linear alkylene groups such as methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, and hexadecamethylene groups; branched alkylene groups such as methylethylene, methylpropylene, ethylethylene, 1,2-dimethylethylene, 1,1-dimethylethylene, 1-ethylpropylene, 2-ethylpropylene, 1,2-dimethylpropylene, 2,2-dimethylpropylene, 1-propylpropylene, 2-propylpropylene, 1-methyl-1-ethylpropylene, 1-methyl-2-ethyl-propylene, 1-ethyl-2-methyl-propylene, 2-methyl-2-ethyl-propylene, 1-methylbutylene, 2-methylbutylene, 3-methylbutylene, 2-ethylbutylene, methylpentylene, ethylpentylene, methylhexylene, methyiheptylene, methyloctylene, methylnonylene, methyldecylene, methylundecylene, methyldodecylene, methyltetradecylene, and methyloctadecylene groups; and the like. Preferred alkylene groups include pentamethylene, hexamethylene, heptamethylene, octamethylene, and nonamethylene.

These divalent groups of atoms may have substituents described later.

Cycloalkylene groups having 3 to 8 carbon atoms include a cyclopropylene group, a cyclobutylene group, a cyclopentylene group, a cyclohexylene group, a cycloheptylene group, a cyclooctylene group, cyclohexenylene, 1,2-cyclohexylenebis(methylene), 1,3-cyclohexylenebis(methylene), 1,4-cyclohexylenebis(methylene), and the like. Preferred cycloalkylene groups include a cyclohexylene group, a cycloheptylene group, a cyclooctylene group, a cyclohexenylene, 1,2-cyclohexylenebis(methylene), 1,3-cyclohexylenebis(methylene), and 1,4-cyclohexylenebis(methylene).

These divalent groups of atoms may have substituents described later.

Examples of the linear or branched alkenylene group having 2 to 20 carbon atoms include vinylene, 1-methylvinylene, propenylene, 1-butenylene, 2-butenylene, 1-pentenylene, and 2-pentenylene groups, and the like. These divalent groups of atoms may have substituents described later.

Examples of the cycloalkenylene group having 3 to 20 carbon atoms include cyclopropenylene, cyclobutenylene, cyclopentenylene, cyclohexenylene, and cyclooctenylene groups, and the like. These divalent groups of atoms may have substituents described later.

Examples of the linear or branched alkynylene group having 2 to 20 carbon atoms include ethynylene, propynylene, 3-methyl-1-propynylene, butynylene, 1,3-butadiynylene, 2-pentynylene, 2-pentynylene, 2,4-pentadiynylene, 2-hexynylene, 1,3,5-hexatriynylene, 3-heptynylene, 4-octynylene, 4-nonynylene, 5-decynylene, 6-undecynylene, and 6-dodecynylene groups, and the like. These divalent groups of atoms may have substituents described later.

Examples of the arylene group having 6 to 20 carbon atoms include phenylenes (o-phenylene, m-phenylene, and p-phenylene), biphenylene, naphthylene, binaphthylene, anthracenylene, and phenanthrylene groups, and the like. These divalent groups of atoms may have substituents described later.

Arylalkylene groups having 8 to 20 carbon atoms include those having a structure of -alkylene-arylene-alkylene-, and preferred specific examples include those having —CH$_2$—Z—CH$_2$— (where Z is a divalent group derived from benzene, naphthalene, biphenyl, or diphenylmethane), for example, phenylenebis(methylenes) (1,2-phenylenebis(methylene), 1,3-phenylenebis(methylene), and 1,4-phenylenebis(methylene)), naphthalenebis(methylene), biphenylenebis(methylene), and the like. Further preferred is 1,3-phenylenebis(methylene). These divalent groups of atoms may have substituents described later.

The heteroalkylene group having 1 to 20 carbon atoms means a group which is the same as the above-described alkylene group, except that one or more, preferably one to five of the carbon atoms in the main chain of the alkylene group are substituted with heteroatoms such as oxygen atoms, sulfur atoms, nitrogen atoms, and phosphorus atoms. Examples thereof include oxa (or thia) alkylene, dioxa (or dithia) alkylene, alkyleneoxy, alkylenethio, alkylenedioxy, alkylenedithio, azaalkylene, diazaalkylene, phosphaalkylene, diphosphaalkylene, and the like. These divalent groups of atoms may have substituents described later.

The heteroarylene group having 2 to 20 carbon atoms means a group which is the same as the above-described arylene group, except that one or more, preferably one to five of the carbon atoms in the arylene group are substituted with heteroatoms such as oxygen atoms, sulfur atoms, nitrogen atoms, and phosphorus atoms. Specific examples of the heteroarylene group include divalent groups derived from phenanthrene, pyrrole, pyrazine, pyridine, pyrimidine, indoline, isoindoline, quinoline, isoquinoline, quinoxaline, carbazole, phenylcarbazole, phenanthridine, acridine, furan, benzofuran, isobenzofuran, dibenzofuran, phenyldibenzofuran, diphenyldibenzofuran, thiophene, phenylthiophene, diphenylthiophene, benzothiophene, dibenzothiophene, phenylbenzothiophene, diphenylbenzothiophene, phenyldibenzothiophene, benzothiazole, and the like. Preferred are divalent groups derived from furan, quinoline, isoquinoline, and phenylcarbazole. These divalent groups of atoms may have substituents described later.

The heteroarylalkylene group having 3 to 20 carbon atoms means a group which is the same as the above-described arylalkylene group, except that one or more, desirably, one to five of the carbon atoms in the arylalkylene group are substituted with heteroatoms such as oxygen atoms, sulfur atoms, nitrogen atoms, and phosphorus atoms. Preferred examples include those having a structure of —$CH_2$—Z—$CH_2$— (where Z is a divalent group derived from furan, pyrrole, thiophene, pyridine, pyrazole, or imidazole). These divalent groups of atoms may have substituents described later.

The divalent groups of atoms including the phenylenevinylene group, the polyfluorene diyl group, the polythiophene diyl group, the dialkylsilane diyl group, and the diarylsilane diyl group may have substituents described later.

Examples of substituents which may be present in the divalent group of atoms represented by L include alkyl groups, alkenyl groups, alkynyl groups, aryl groups, aliphatic heterocyclic groups, aromatic heterocyclic groups, alkoxy groups, alkylenedioxy groups, aryloxy groups, aralkyloxy groups, heteroaryloxy groups, acyl groups, substituted amino groups (for example, alkyl-substituted amino groups, aryl-substituted amino groups, aralkyl-substituted amino groups, acyl-substituted amino groups, alkoxycarbonyl-substituted amino groups, and the like), alkoxycarbonyl groups, aryloxycarbonyl groups, aralkyloxycarbonyl groups, sulfo groups, cyano groups, nitro groups, halogenated alkyl groups, halogen atoms, and the like.

The alkyl groups may be linear, branched, or cyclic, and examples thereof include alkyl groups having 1 to 15 carbon atoms, preferably 1 to 10 carbon atoms, and more preferably 1 to 6 carbon atoms. Specific examples thereof include methyl groups, ethyl groups, n-propyl groups, isopropyl groups, n-butyl groups, 2-butyl groups, isobutyl groups, tert-butyl groups, n-pentyl groups, 2-pentyl groups, tert-pentyl groups, 2-methylbutyl groups, 3-methylbutyl groups, 2,2-dimethylpropyl groups, n-hexyl groups, 2-hexyl groups, 3-hexyl groups, 2-methylpentyl groups, 3-methylpentyl groups, 4-methylpentyl groups, 2-methylpentan-3-yl groups, cyclopropyl groups, cyclobutyl groups, cyclopentyl groups, cyclohexyl groups, and the like.

The alkenyl groups may be linear or branched, and examples thereof include alkenyl groups having 2 to 15 carbon atoms, preferably 2 to 10 carbon atoms, and more preferably 2 to 6 carbon atoms. Specific examples thereof include vinyl groups, 1-propenyl groups, allyl groups, 1-butenyl groups, 2-butenyl groups, 1-pentenyl groups, 2-pentenyl groups, hexenyl groups, and the like.

The alkynyl groups may be linear or branched, and examples thereof include alkynyl groups having 2 to 15 carbon atoms, preferably 2 to 10 carbon atoms, and more preferably 2 to 6 carbon atoms. Specific examples thereof include ethynyl groups, 1-propynyl groups, 2-propynyl groups, 1-butynyl groups, 3-butynyl groups, pentynyl groups, hexynyl groups, and the like.

Examples of the aryl groups include aryl groups having 6 to 14 carbon atoms, and specific examples thereof include phenyl groups, naphthyl groups, anthryl groups, phenanthrenyl groups, biphenyl groups, and the like.

Examples of the aliphatic heterocyclic groups include 5- to 8-membered, preferably 5- or 6-membered monocyclic aliphatic heterocyclic groups having 2 to 14 carbon atoms and containing at least one, preferably one to three heteroatoms such as nitrogen atoms, oxygen atoms, and sulfur atoms and aliphatic heterocyclic groups obtained by condensation of 5- to 8-membered, preferably 5 to 6-membered monocyclic aliphatic heterocycles. Specific examples of the aliphatic heterocyclic groups include 2-oxopyrrolidino groups, piperidino groups, piperazinyl groups, morpholino groups, tetrahydrofuryl groups, tetrahydropyranyl groups, tetrahydrothienyl groups, perhydronaphthyl groups, and the like.

Examples of the aromatic heterocyclic groups include 5- to 8-membered, preferably 5- or 6-membered monocyclic aromatic heterocyclic groups having 2 to 15 carbon atoms and containing at least one, preferably one to three heteroatoms such as nitrogen atoms, oxygen atoms, and sulfur atoms, and aromatic heterocyclic groups obtained by condensation of 5- to 8-membered, preferably 5 to 6-membered monocycles. Specific examples thereof include pyrrolyl groups, furyl groups, thienyl groups, pyridyl groups, pyrimidyl groups, pyrazyl groups, pyridazyl groups, pyrazolyl groups, imidazolyl groups, oxazolyl groups, thiazolyl groups, indolyl groups, benzofuryl groups, benzothienyl groups, quinolyl groups, isoquinolyl groups, quinoxalyl groups, phthalazyl groups, quinazolyl groups, naphthyridyl groups, cinnolyl groups, benzoimidazolyl groups, benzoxazolyl groups, benzothiazolyl groups, tetrahydronaphthyl groups, and the like.

The alkoxy groups may be linear, branched, or cyclic, and examples thereof include alkoxy groups having 1 to 6 carbon atoms. Specific examples thereof include methoxy groups, ethoxy groups, n-propoxy groups, isopropoxy groups, n-butoxy groups, 2-butoxy groups, isobutoxy groups, tert-butoxy groups, n-pentyloxy groups, 2-methylbutoxy groups, 3-methylbutoxy groups, 2,2-dimethylpropyloxy groups, n-hexyloxy groups, 2-methylpentyloxy groups, 3-methylpentyloxy groups, 4-methylpentyloxy groups, 5-methylpentyloxy groups, cyclohexyloxy groups, and the like.

Examples of the alkylenedioxy groups include alkylenedioxy groups having 1 to 3 carbon atoms, and specific examples thereof include methylenedioxy groups, ethylenedioxy groups, propylenedioxy groups, and the like.

Examples of the aryloxy groups include aryloxy groups having 6 to 14 carbon atoms, and specific examples thereof include phenyloxy groups, naphthyloxy groups, anthryloxy groups, benzyloxy groups, and the like.

Examples of the aralkyloxy groups include aralkyloxy groups having 7 to 12 carbon atoms, and specific examples thereof include benzyloxy groups, 2-phenylethoxy groups, 1-phenylpropoxy groups, 2-phenylpropoxy groups, 3-phenylpropoxy groups, 1-phenylbutoxy groups, 2-phenylbutoxy groups, 3-phenylbutoxy groups, 4-phenylbutoxy groups, 1-phenylpentyloxy groups, 2-phenylpentyloxy groups, 3-phenylpentyloxy groups, 4-phenylpentyloxy groups, 5-phenylpentyloxy groups, 1-phenylhexyloxy groups, 2-phenylhexyloxy groups, 3-phenylhexyloxy groups, 4-phenylhexyloxy groups, 5-phenylhexyloxy groups, 6-phenylhexyloxy groups, and the like.

Examples of the heteroaryloxy groups include heteroaryloxy groups having 2 to 14 carbon atoms and containing at least one, preferably one to three heteroatoms such as nitrogen atoms, oxygen atoms, and sulfur atoms. Specific examples thereof include 2-pyridyloxy groups, 2-pyrazyloxy groups, 2-pyrimidyloxy groups, 2-quinolyloxy groups, and the like.

The acyl groups may be linear, branched, or cyclic, and examples thereof include acyl groups having 2 to 10 carbon atoms. Specific examples thereof include acetyl groups, propanoyl groups, butyryl groups, pivaloyl groups, benzoyl groups, and the like.

The alkoxycarbonyl groups may be linear, branched, or cyclic, and examples thereof include alkoxycarbonyl groups having 2 to 19 carbon atoms. Specific examples thereof include methoxycarbonyl groups, ethoxycarbonyl groups, n-propoxycarbonyl groups, isopropoxycarbonyl groups, n-butoxycarbonyl groups, tert-butoxycarbonyl groups, pentyloxycarbonyl groups, hexyloxycarbonyl groups, 2-ethylhexyloxycarbonyl groups, lauryloxycarbonyl groups, stearyloxycarbonyl groups, cyclohexyloxycarbonyl groups, and the like.

Examples of the aryloxycarbonyl groups include aryloxycarbonyl groups having 7 to 20 carbon atoms. Specific examples thereof include phenoxycarbonyl groups, naphthyloxycarbonyl groups, and the like. Examples of the aralkyloxycarbonyl groups include aralkyloxycarbonyl groups having 8 to 15 carbon atoms, and specific examples thereof include benzyloxycarbonyl groups, phenylethoxycarbonyl groups, 9-fluorenylmethyloxycarbonyl, and the like.

Examples of the aralkyloxycarbonyl groups include aralkyloxycarbonyl groups having 8 to 15 carbon atoms, and specific examples thereof include benzyloxycarbonyl groups, phenylethoxycarbonyl groups, 9-fluorenylmethyloxycarbonyl groups, and the like.

The substituted amino groups include amino groups in which one or two hydrogen atoms are substituted with substituents such as the above-described alkyl groups, the above-described aryl groups, and protective groups for amino group. As the protective groups, any groups used as amino-protecting groups can be used (see, for example, "PROTECTIVE GROUPS IN ORGANIC SYNTHESIS THIRD EDITION (JOHN WILEY & SONS, INC. (1999))). Specific examples of the amino-protecting groups include aralkyl groups, acyl groups, alkoxycarbonyl groups, aryloxycarbonyl groups, aralkyloxycarbonyl groups, and the like.

Specific examples of the amino groups substituted by an alkyl group(s) include mono- or di-alkylamino groups such as N-methylamino groups, N,N-dimethylamino groups, N,N-diethylamino groups, N,N-diisopropylamino groups, and N-cyclohexylamino groups.

Specific examples of the amino groups substituted by an aryl group(s) include mono- or di-arylamino groups such as N-phenylamino groups, N-(3-tolyl)amino groups, N,N-diphenylamino groups, N,N-di(3-tolyl)amino groups, N-naphthylamino groups, and N-naphthyl-N-phenylamino groups.

Specific examples of the amino groups substituted by an aralkyl group(s), i.e., amino group-substituted by aralkyl groups include mono- or di-aralkylamino groups such as N-benzylamino groups and N,N-dibenzylamino groups.

Specific examples of the amino groups substituted by an acyl group(s) include formylamino groups, acetylamino groups, propionylamino groups, pivaloylamino groups, pentanoylamino groups, hexanoylamino groups, benzoylamino groups, and the like.

Specific examples of the amino groups substituted by an alkoxycarbonyl group(s) include methoxycarbonylamino groups, ethoxycarbonylamino groups, n-propoxycarbonylamino groups, n-butoxycarbonylamino groups, tert-butoxycarbonylamino groups, pentyloxycarbonylamino groups, hexyloxycarbonylamino group, and the like.

Specific examples of the amino groups substituted by an aryloxycarbonyl group(s) include phenoxycarbonylamino groups, naphthyloxycarbonylamino groups, and the like.

Specific examples of the amino groups substituted by an aralkyloxycarbonyl group(s) include benzyloxycarbonylamino groups and the like.

The halogenated alkyl groups include alkyl groups having 1 to 4 carbon atoms in which hydrogen atoms are substituted with halogen atoms described later, and examples thereof include fluoromethyl groups, difluoromethyl groups, trifluoromethyl groups, trichloromethyl groups, and the like.

The halogen atoms include fluorine atoms, chlorine atoms, bromine atoms, iodine atoms, and the like.

L is preferably an optionally substituted 1,3-phenylenebis(methylene) group represented by general formula (II). In the formula, X represents a hydrogen atom, an optionally substituted alkyl group having 1 to 10 carbon atoms, an optionally substituted alkoxy group having 1 to 10 carbon atoms, an optionally substituted aryl group, an optionally substituted allyl group, or a substituted amino group. These groups are the same as the groups described above. The substituted amino group may be an amino group in which two hydrogen atoms are substituted with substituents such as any ones of the above-described alkyl groups, the above-described aryl groups, protective groups for amino group, and the like. The protective groups are the same as those of the above-described substituted amino groups:

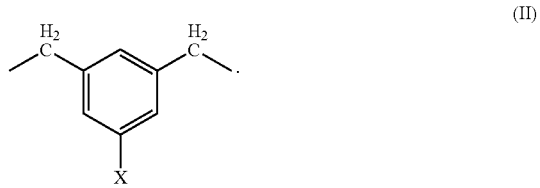

(II)

Representative examples of the compound represented by general formula (I) are the following compounds (2-1) to (2-12) shown below.

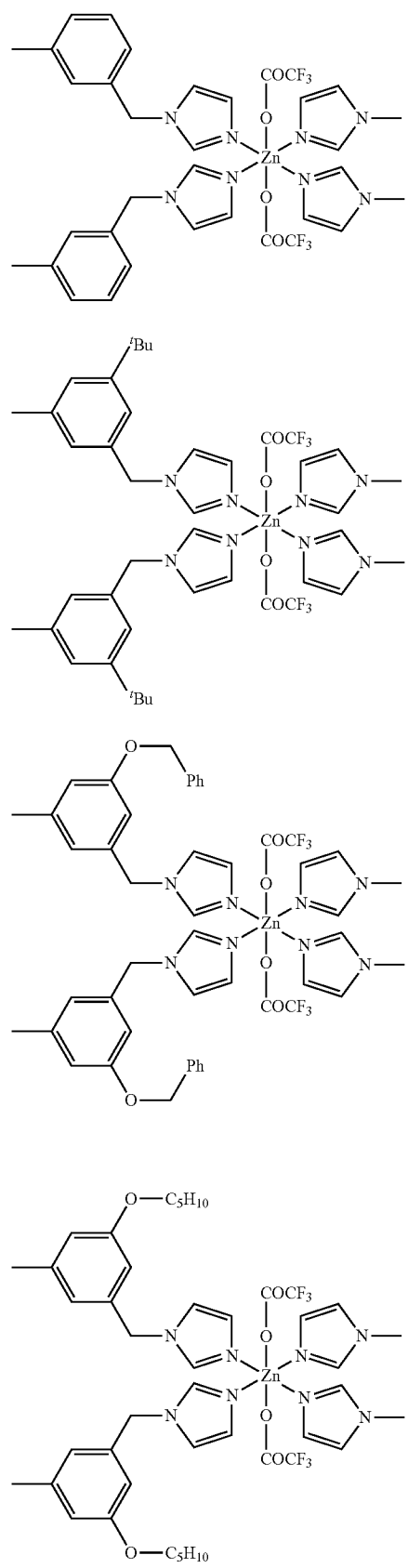
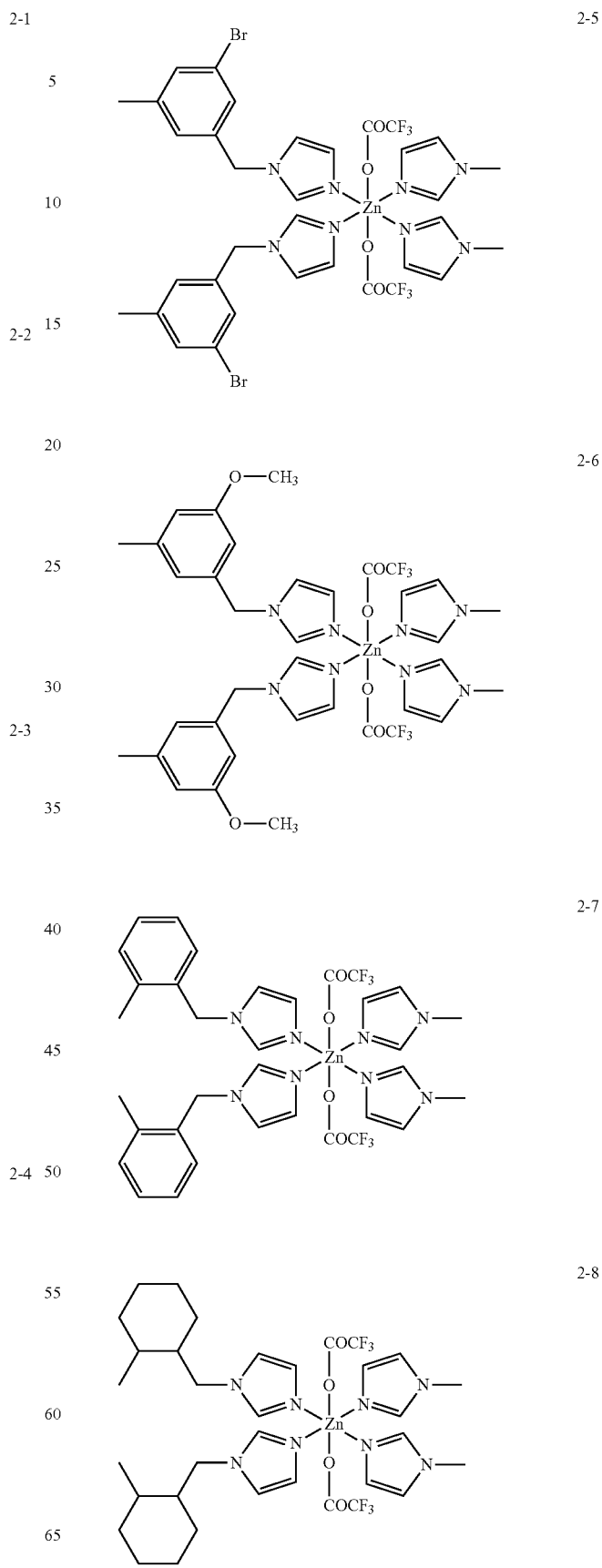

2-9

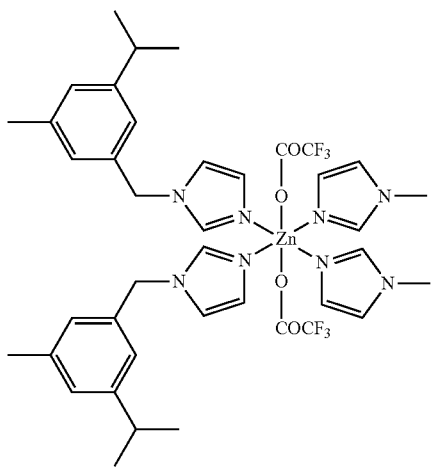

2-10

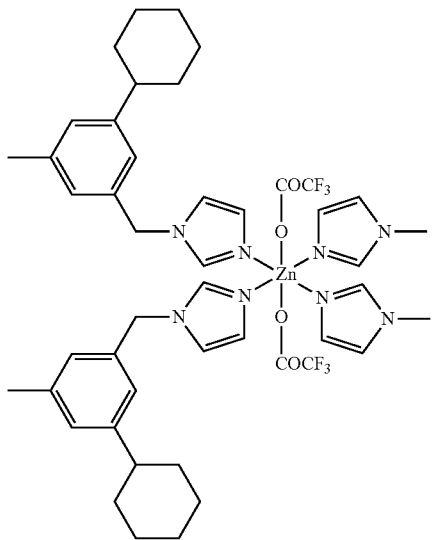

2-11

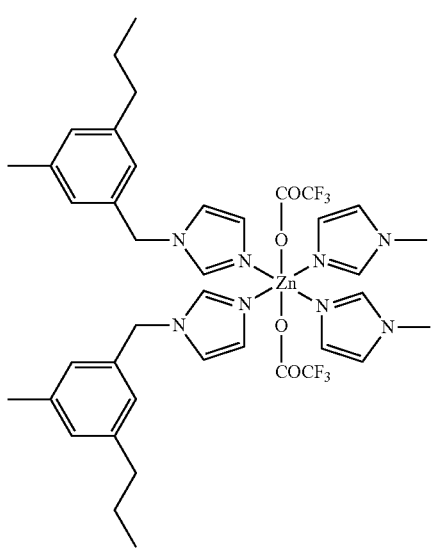

2-12

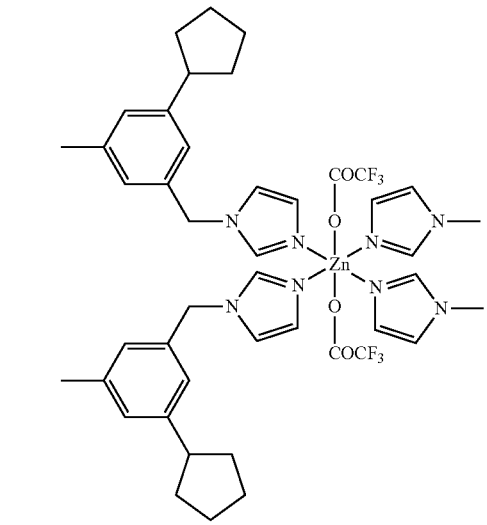

The zinc complex represented by general formula (I) can be obtained by reacting a compound represented by general formula (V) (ligand):

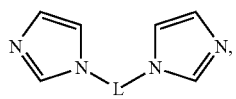 (V)

wherein L represents a linker moiety, with
the general formula (III):

$$Zn(OCOR^{1a})_2 \cdot xH_2O \quad (III),$$

wherein $R^{1a}$ represents an alkyl group having 1 to 4 carbon atoms and optionally having a halogen atom(s) and optionally having a halogen atom(s), and x represents any number of 0 or greater, or
the general formula (IV):

$$Zn_4O(OCOR^{1b})_6 R^{1b}COOH)_n \quad (IV),$$

wherein $R^{1b}$ represents an alkyl group having 1 to 4 carbon atoms and optionally having a halogen atom(s) and optionally having a halogen atom(s), and n represents 0 to 1.

Examples of the alkyl group having 1 to 4 carbon atoms and optionally having a halogen atom(s) include a trichloromethyl group; a tribromomethyl group; perfluoroalkyl groups such as a trifluoromethyl group, a pentafluoroethyl group, a heptafluoropropyl group, and a heptafluoroisopropyl group; and the like. Of these groups, a preferred group is a trifluoromethyl ($CF_3$) group.

x represents any number of 0 or greater, and is preferably in the range from 0 to 8, and further preferably in the range from 0 to 3.

By single-crystal X-ray crystallography, the obtained zinc complex was identified as a crystal in the form of an infinite chain in which the bonding extend continuously in a one-dimensional direction or two-dimensional directions with an octahedral geometry in which four nitrogen atoms on one side of imidazole groups serving as the ligand are coordinated to one zinc atom, and two carboxylate groups $OCOR^{1a}$ or $OCOR^{1b}$ are coordinated to the zinc atom with trans configuration or cis configuration.

It should be noted that the complex with an octahedral geometry can be obtained when 2 mole equivalents of the ligand is reacted with zinc atoms of the zinc carboxylate compound serving as the raw material. In contrast, when the ligand is 1 equivalent to zinc atoms of the zinc carboxylate compound, a zinc complex with a tetrahedral geometry is obtained, and the zinc complex with a tetrahedral geometry does not have catalytic activity.

Regarding solvents used for the production of the zinc complex of the present invention, solvents which do not affect the formation of the zinc complex of the present invention can be used. Solvents capable of dissolving the zinc carboxylate compound and the ligand can be used. For example, tetrahydrofuran (THF), benzene, toluene, xylene, hexane, heptane, octane, or the like can be used. Preferred are solvents such as toluene, xylene, and THF, and THF is more preferable. In addition, the reaction can also be conducted as a solventless reaction.

The reaction temperature is preferably at or above a temperature at which the zinc carboxylate compound and the ligand can be dissolved, and is 30° C. to 250° C., and more preferably 30° C. to 150° C.

The reaction time is not particularly limited, and the reaction can be conducted in approximately 1 to 45 hours, in general, and preferably in about 2 to 24 hours.

In most cases, the zinc complex obtained during the reaction is insoluble in the solvent, and precipitates. For this reason, after completion of the reaction, the zinc complex can be obtained by filtration or the like. In a case where the zinc complex is dissolved in the reaction solution or other cases, the zinc complex may be taken out by evaporation of the solvent followed by drying.

The zinc complex represented by general formula (I) of the present invention obtained under the above-described conditions is stable in the air, and is more stable than the zinc trifluoroacetate tetranuclear cluster complexes which are described in Japanese Patent Application Publication No. 2009-185033, Domestic Re-publication of PCT International Publication No. 2009-047905, and Japanese Patent Application Publication No. 2011-079810, and which are unstable in the air because of their high hygroscopicity. However, it is preferable to handle the zinc complex of the present invention in the presence of inert gas in which the amount of water is small. The inert gas is, preferably, nitrogen, argon, or the like.

When the zinc complex of the present invention is used as a catalyst, the zinc complex prepared in the presence of a suitable solvent (for example, THF) in advance as described above may be added as a catalyst to the reaction system, or the reaction may be conducted by adding the raw materials, namely, the zinc carboxylate compound represented by general formula (III) or (IV) and the compound represented by general formula (V) (ligand) as a catalyst to the reaction system (in-situ method).

The zinc complex of the present invention enables a selective acylation reaction of or a selective carbonate formation reaction from an alcoholic hydroxy group in a case where a nucleophilic functional group such as an amino group and an alcoholic hydroxy group are simultaneously present in a reaction system.

The case where a nucleophilic functional group such as an amino group and an alcoholic hydroxy group are simultaneously present in a reaction system may be a case of a compound having the amino group and the alcoholic hydroxy group in a single molecule, or may be a case of different compounds. The compound having an amino group and an alcoholic hydroxy group in a single molecule may be an amino alcohol. Meanwhile, the case where the compound having an amino group and the compound having an alcoholic hydroxy group are different may be a case where an amine and an alcohol are simultaneously present in the reaction system.

The amino group may be a primary amino group or a secondary amino group. Meanwhile, the alcoholic hydroxy group may be any one of a primary hydroxy group, a secondary hydroxy group, or a tertiary hydroxy group. The amino alcohol is not particularly limited, as long as the amino alcohol is a compound having an amino group and an alcoholic hydroxy group. Examples of the amino alcohol include open-chain, branched, cyclic, or condensed-cyclic and aliphatic or aromatic amino alcohols and the like.

The zinc complex of the present invention enables a carbonate formation reaction from a carbonate ester and a compound having an alcoholic hydroxy group. The carbonate ester used in this reaction is a generic term for compounds obtainable by substituting one or two of the two hydrogen atoms of carbonic acid $H_2CO_3$ with alkyl or aryl groups. From the viewpoint of handling, compounds in which two hydrogen atoms are substituted are preferable. As the carbonate ester, a dialkyl carbonate or a diaryl carbonate is used. Preferred specific examples of the carbonate ester used include dimethyl carbonate, diethyl carbonate, methyl ethyl carbonate, methyl phenyl carbonate, ethyl phenyl carbonate, and diphenyl carbonate. Of these carbonate esters, dimethyl carbonate is preferable.

Compounds having an alcoholic hydroxy group include compounds which are linear or cyclic aliphatic hydrocarbons having one, two, or multiple hydroxy groups. In addition, as the compounds having two or more hydroxy groups, cyclic carbonates can be obtained by, for example, reacting a diol compound and a carbonate ester by using the present catalyst.

The zinc complex of the present invention enables a deacylation reaction of a compound having an ester group. The compound having an ester group used in this reaction may be an aliphatic carboxylate ester, an aromatic carboxylate ester, or the like. The ester may be an ester derived from a monocarboxylic acid or a polycarboxylic acid.

Compounds having an ester group used in this reaction include alkyl esters such as methyl esters, ethyl esters, propyl esters, butyl esters, hexyl esters, and octyl esters; aryl esters such as phenyl esters, biphenyl esters, and naphthyl esters; aralkyl esters such as benzyl esters and 1-phenethyl esters; and the like of carboxylic acids described below. Preferred are methyl esters of the carboxylic acids described below.

The aliphatic carboxylic acid may be a monocarboxylic or polycarboxylic acid having 2 to 30 carbon atoms. Specific examples thereof include acetic acid, propionic acid, butyric acid, valeric acid, hexanoic acid, heptanoic acid, octanoic acid, nonanic acid, decanoic acid, dodecanoic acid, lauric acid, myristic acid, palmitic acid, stearic acid, oleic acid, oxalic acid, propanedicarboxylic acid, butanedicarboxylic acid, hexanedicarboxylic acid, sebacic acid, acrylic acid, and the like.

In addition, these aliphatic carboxylic acids may be substituted by substituents. The substituents include alkyl groups, alkoxy groups, halogen atoms, amino groups, aryl groups, heteroaryl groups, aralkyl groups, silyloxy groups, hydroxy groups, and the like.

The aromatic carboxylic acid may be benzoic acid, naphthalenecarboxylic acid, pyridinecarboxylic acid, quinolinecarboxylic acid, furancarboxylic acid, thiophenecarboxylic acid, or the like.

In addition, these aromatic carboxylic acids may be substituted by any of the above-described alkyl groups, alkoxy groups, halogen atoms, amino groups, aryl groups, heteroaryl groups, aralkyl groups, hydroxy groups, and the like.

The amount of the zinc complex used as a catalyst in each reaction of the present invention is not particularly limited, but is generally the ratio of zinc atoms is 0.001 to 0.9 mol, more preferably 0.001 to 0.3 mol, further preferably 0.001 to 0.1 mol relative to 1 mol of a raw material.

Each reaction is conducted in a solvent, in general. Specific examples of the solvent include, but are not particularly limited to, aromatic solvents such as toluene, xylene, and benzene chloride; aliphatic hydrocarbon solvents such as hexane, heptane, and octane; ether solvents such as diethyl ether, diisopropyl ether, tert-butyl methyl ether, tetrahydrofuran, and 1,4-dioxane; amide solvents such as dimethylformamide (DMF), dimethylacetamide (DMAc), and N-methylpyrrolidone (NMP); dimethyl sulfoxide (DMSO); and the like. In addition, when the substrate used is a liquid, and the solubility of the zinc complex in the substrate is high, it is not necessary to use a solvent.

Various reactions using the zinc complex of the present invention as a catalyst can be conducted in the air or in an inert gas atmosphere of nitrogen gas, argon gas, or the like.

The reaction time is not particularly limited, and in general, the reaction can be conducted in approximately 1 to 45 hours, and preferably about 6 to 18 hours.

The reaction temperature is not particularly limited, and the reaction is conducted at room temperature to approximately 180° C., preferably 50 to 150° C., more preferably approximately 80 to 150° C. These conditions may be changed, as appropriate, according to the kinds and the amounts of the raw material used and the like.

The zinc complex of the present invention is dissolved during a reaction at high temperature. However, when the temperature is cooled to room temperature after completion of the reaction, the zinc complex is precipitated again as a solid. For this reason, the zinc complex can be easily recovered by filtration. It has been found that the recovered zinc complex has the same structure as that before the reaction, and the catalytic activity is not lowered even when the zinc complex is reused repeatedly.

Another technique for the recovery and reuse other than the filtration is as follows. Specifically, in a case where the substrate and the target product have low-boiling points, the reaction liquid is directly concentrated after completion of the reaction, so that the catalyst (zinc complex) can be easily recovered and reused.

As described above, the catalyst comprising the zinc complex of the present invention does not decompose or lose its activity with the progress of the reaction as in the case of already reported catalysts, but is extremely stable and further exhibits a high activity.

EXAMPLES

Hereinafter, the present invention will be described in detail based on Examples. However, the present invention is not limited thereto. Note that analytical instruments were as follows. In addition, all operations in Examples were conducted in an argon atmosphere.

NMR: Varian Unity (400 MHz), Bruker Advanced III (500 MHz)

Reference Example 1

Synthesis of Ligand (A)

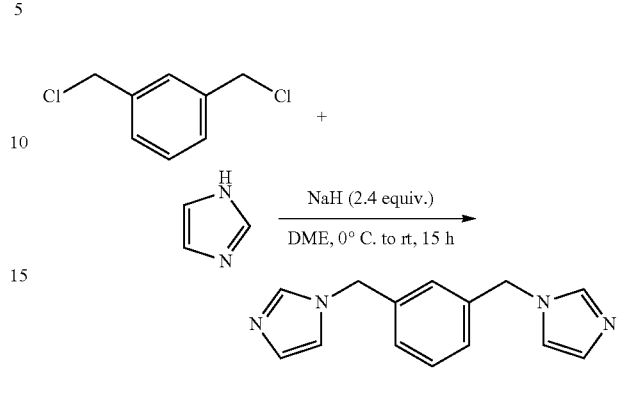

To a solution of imidazole (408.7 mg, 6.0 mmol) in 10 mL of dimethoxyethane (DME), sodium hydride (60% in mineral oil, 309.3 mg, 7.73 mmol) was gradually added at 0° C. Subsequently, dichloro-m-xylene (4.87 mmol) was added, followed by stirring at room temperature for 15 hours. A 20% aqueous sodium hydroxide solution was added, followed by extraction with ethyl acetate. The obtained organic layer was washed with saturated aqueous sodium chloride, and dried over anhydrous magnesium sulfate. The solvent was evaporated, and then the obtained crude product was purified by flash column chromatography ($CH_2Cl_2$/MeOH=20/1) to obtain the target product as a colorless solid in a yield of 98%.

1H NMR (500 MHz, CDCl3) δ 7.53 (s, 2H, NCHN), 7.35 (t, J=2.5 Hz, 1H, Ar), 7.10 (s, 2H, Ar), 7.09 (s, 2H, CH2NCHCH), 6.92 (s, 1H, Ar), 6.88 (s, 2H, CH2NCHCH), 5.10 (s, 4H, NCH2)

Reference Example 2

Synthesis of Ligand (B)

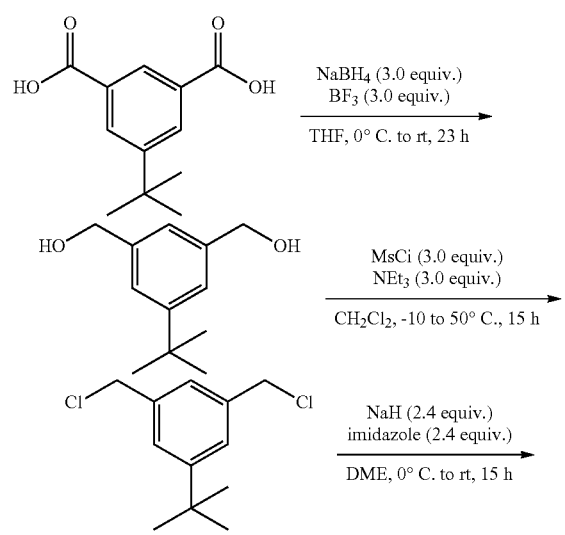

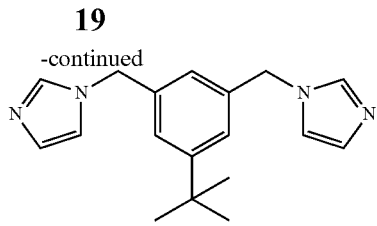

(a) Synthesis of (5-(tert-Butyl)-1,3-phenylene)dimethanol

To tetrahydrofuran (THF) (50 mL), 5-tert-butyl-isophthalic acid (2.22 g, 10.0 mmol) and sodium borohydride (1.17 g, 30.9 mmol) were added. To this suspension, BF3.OEt$_2$ (3.70 mL, 30.0 mmol) was gradually added at 0° C., followed by stirring at room temperature for 23 hours. The reaction was quenched by adding water, followed by extraction with ethyl acetate. The obtained organic layer was washed with 1 M aqueous hydrochloric acid and saturated aqueous sodium hydrogen carbonate in this order, and dried over anhydrous sodium sulfate. The solvent was evaporated, and then the obtained crude product was purified by flash column chromatography (CH$_2$Cl$_2$/MeOH=30/1 to 20/1) to obtain the target product as a colorless solid in a yield of 95%.

1H NMR (400 MHz, CDCl3) δ 7.33 (s, 2H, Ar), 7.20 (s, 1H, Ar), 4.70 (s, 4H, CH2), 1.33 (s, 9H, CH3)

(b) Synthesis of 1-(tert-Butyl)-3,5-bis(chloromethyl)benzene

To dichloromethane (15 mL), (5-(tert-butyl)-1,3-phenylene)dimethanol (5.0 mmol) obtained in (a) described above and triethylamine (15.0 mmol) were added. To this solution, methanesulfonyl chloride (14.9 mmol) was gradually added at −15° C., followed by stirring for 40 minutes, and then by stirring at 50° C. for 14 hours. The reaction liquid was washed with 1 M aqueous hydrochloric acid, saturated aqueous sodium hydrogen carbonate, and saturated aqueous sodium chloride in this order, and dried over anhydrous magnesium sulfate. The solvent was evaporated, and then the obtained crude product was purified by flash column chromatography (hexane/AcOEt=30/1) to obtain the target product as a colorless solid in a yield of 84%.

1H NMR (400 MHz, CDCl3) 7.35 (s, 2H, Ar), 7.25 (s, 1H, Ar), 4.58 (s, 4H, CH2), 1.33 (s, 9H, CH3)

(c) Synthesis of Ligand (B)

By using 1-(tert-butyl)-3,5-bis(chloromethyl)benzene obtained in (b) described above and imidazole, the target product was obtained as a colorless solid in a yield of 91% by the same method as in Reference Example 1.

1H NMR (400 MHz, CDCl3) δ 7.52 (s, 2H, NCHN), 7.10 (d, J=6.4 Hz, 2H, Ar), 7.10 (d, J=6.4 Hz, 2H, CH2NCHCH), 6.88 (s, 2H, CH2NCHCH), 6.70 (s, 1H, Ar), 5.08 (s, 4H, CH2)

Example 1

Production of Zinc Complex

Zinc complexes of the present invention were prepared by reacting predetermined amounts of ligands A and B with a tetranuclear zinc cluster complex Zn$_4$(OCOCF$_3$)$_6$O as shown in the following reaction formulae.

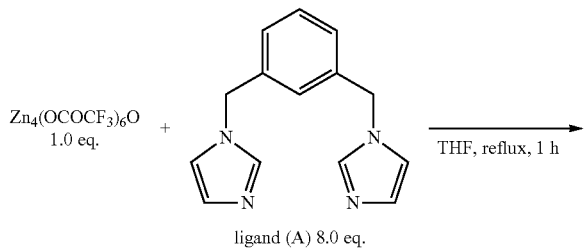

(1)

Zinc Complex A

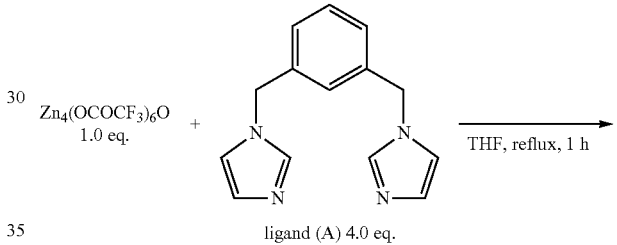

(2)

Zinc Complex B

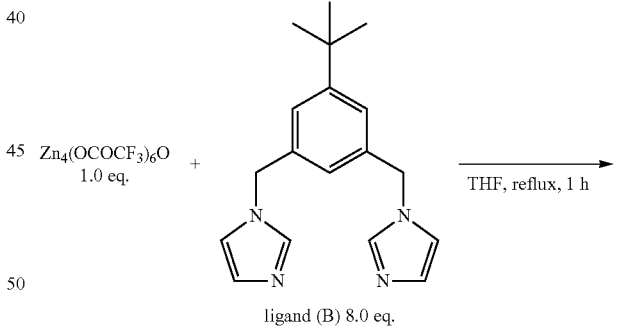

(3)

Zinc Complex C

Each of the obtained zinc complexes was subjected to single-crystal X-ray crystallography. Table 1 shows the analysis data.

TABLE 1

Crystal Data and Data Colestion Parameters[a, b]

|  | a | b | c |
|---|---|---|---|
| empirical formula | C$_{32}$H$_{28}$F$_6$N$_8$O$_4$Zn | C$_{30}$H$_{30}$F$_3$N$_4$O$_6$Zn | C$_{40}$H$_{44}$F$_6$N$_8$O$_4$Zn |
| formula weight | 767.99 | 664.95 | 880.20 |

TABLE 1-continued

Crystal Data and Data Colestion Parameters[a, b]

|  | a | b | c |
|---|---|---|---|
| crystal system | triclinic | triclinic | monoclinic |
| space group | P-1 | P-1 | $P2_1/n$ (No. 14) |
| a, Å | 8.815(4) | 9.747(2) | 14.5768(12) |
| b, Å | 9.287(5) | 11.299(2) | 8.9341(7) |
| c, Å | 11.376(6) | 11.586(2) | 15.9047(13) |
| α, deg. | 82.508(5) | 99.020(2) | — |
| β, deg. | 67.980(5) | 107.884(2) | 103.2940(10) |
| γ, deg. | 67.616(5) | 113.050(2) | — |
| V, Å$^3$ | 798.2(7) | 1059.9(4) | 2015.8(3) |
| Z | 1 | 1 | 2 |
| $D_{calcd}$, g/cm$^{-3}$ | 1.598 | 1.042 | 1.450 |
| μ [Mo-Kα], mm$^{-1}$ | 0.71069 | 0.71073 | 0.71073 |
| T, K | 90 | 90 | 90 |
| crystal size, mm |  |  |  |
| 2 θ $_{max}$, deg. | 56.6 | 56.5 | 57.1 |
| no. of reflections measured | 4204 | 5940 | 10987 |
| unique data ($R_{int}$) | 3332 (0.0390) | 4547 (0.0163) | 4583 (0.0165) |
| data/restraints/parameters | 3332/0/246 | 4547/0/355 | 4583/0/271 |
| R1 (I > 2.0 σ (I)) | 0.0864 | 0.0272 | 0.0394 |
| wR2 (I > 2.0 σ (I)) | 0.2019 | 0.1001 | 0.1612 |
| R1 (all data) |  | 0.0282 | 0.0411 |
| wR2 (all data) |  | 0.1017 | 0.1672 |
| GOF on F$^2$ | 0.995 | 0.936 | 1.549 |
| Δ ρ, e Å-3 | 4.450, −5.140 | 0.447, −0.480 | 1.222, −1.053 |

[a]R1= (Σ | |Fo| − |Fc| |)/(Σ |Fo|).
[b]wR2 = [{Σ w(Fo$^2$ − Fc$^2$)$^2$}/{Σ w(Fo$^4$)}]$^{1/2}$.

Figure 2:
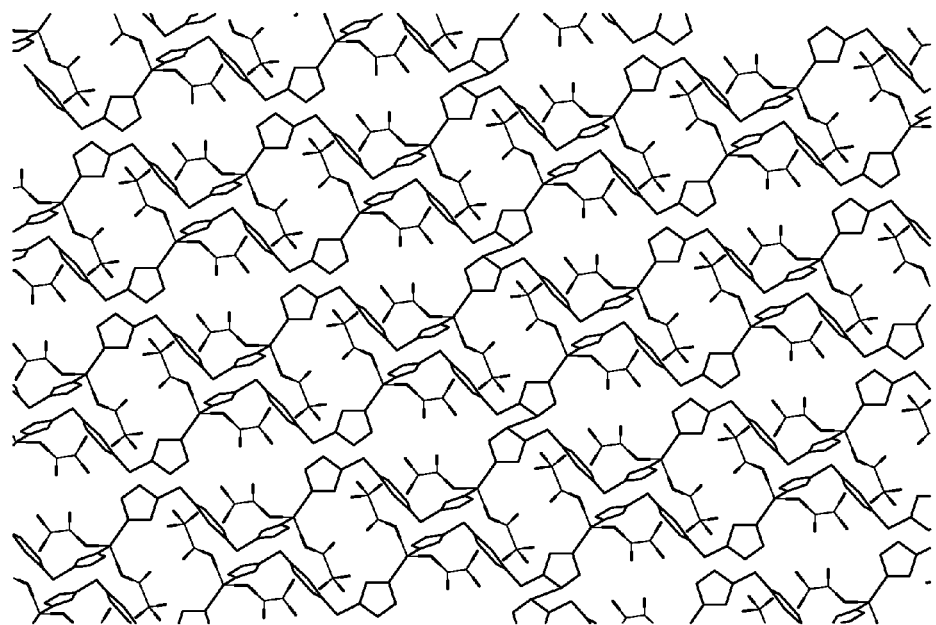
FIG. 2 shows a result of X-ray crystallography of a zinc complex B with a tetrahedral geometry.
Figure 2:
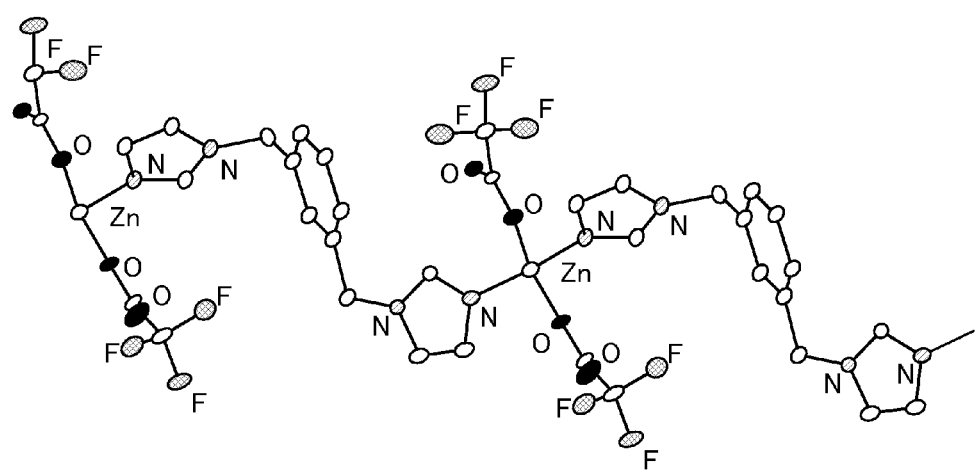
Figure 3:
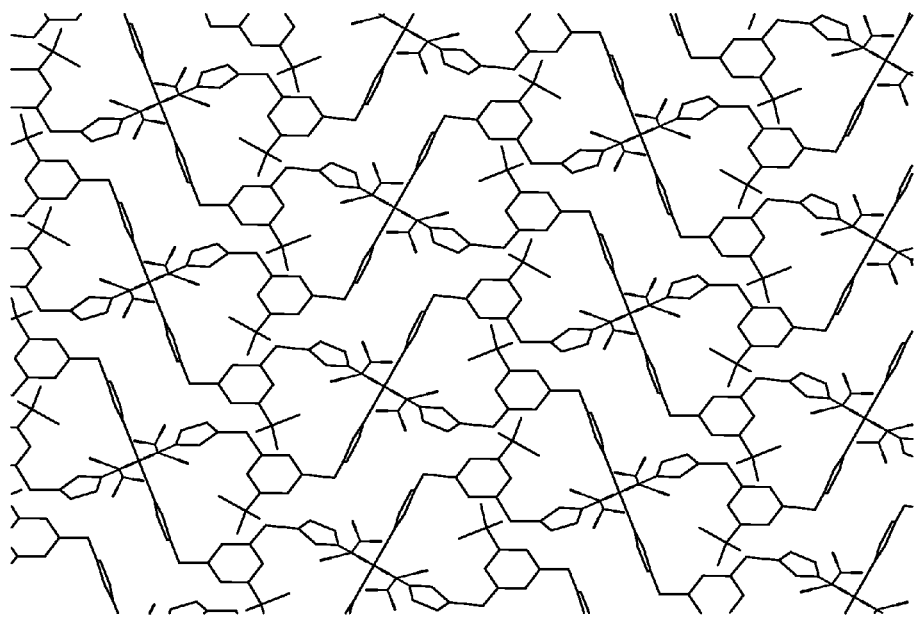
FIG. 3 shows a result of X-ray crystallography of a zinc complex C with an octahedral geometry of the present invention.
Figure 3:
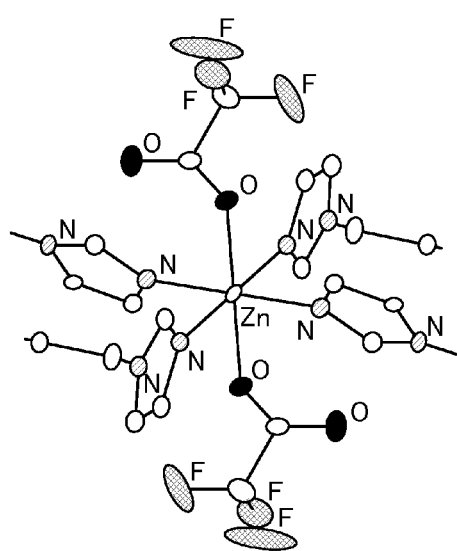

In addition, FIGS. 1 to 3 show the obtained results of the single crystal X-ray structures.

The single-crystal X-ray crystallography shows that each of the zinc complex A and the zinc complex C of the present invention has an octahedral geometry in which four nitrogen atoms on one side of the imidazole groups are coordinated to one zinc atom and two groups of atoms CF$_3$COO are coordinated to the zinc atom with trans configuration. In addition, it has been found that the zinc complex A is an infinite chain complex in which the bonding extends continuously in a one-dimensional direction, and that the zinc complex C is an infinite chain complex in which the bonding extends continuously in two-dimensional directions. In contrast, the zinc complex B (control) was an one-dimensional infinite complex with a tetrahedral geometry in which two nitrogen atoms on one side of imidazole groups are coordinated to one zinc atom and two groups of atoms, namely, CF$_3$COO groups are coordinated to the zinc atom with trans configuration.

Figure 4:
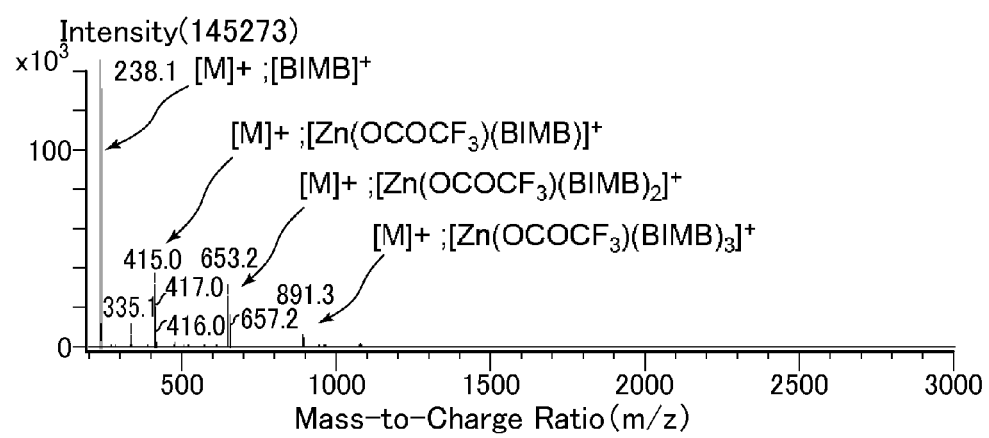
FIG. 4 shows an MS measurement result of the zinc complex A.
Figure 5:
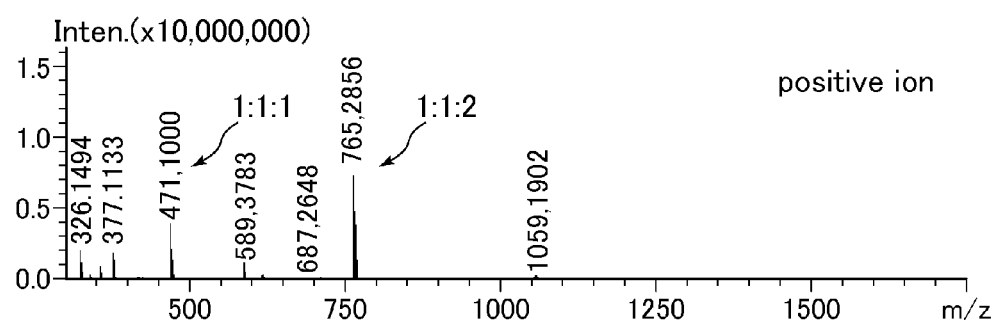
FIG. 5 shows an MS measurement result of the zinc complex C.

FIG. 4 shows an MS measurement result of the zinc complex A. In addition, FIG. 5 shows an MS measurement result of the zinc complex C. Each ratio represents the ratio between zinc, trifluoroacetic acid, and the ligand having imidazolyl groups.

Note that the MS measurement was conducted with the following instrument.

MS (direct introduction (direct inlet, direct infusion)) Zinc complex A: JMS-T100GCV (JEOL Ltd.), ionization mode: FD Zinc complex C: LC-MS-IT-TOF (Shimadzu Corporation), ionization mode: ESI Example 2

Transesterification Reaction

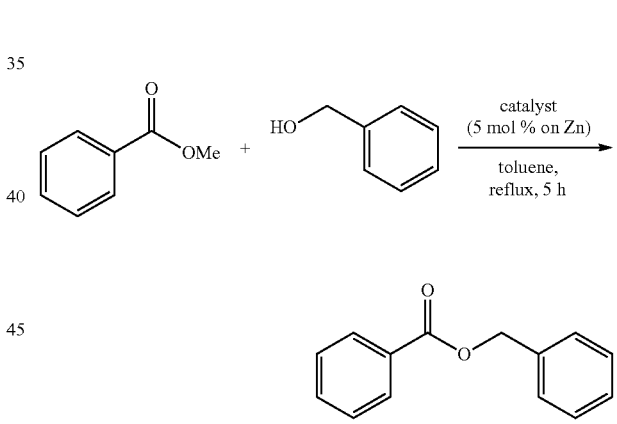

By using the zinc complex A prepared in Example 1 at a catalyst ratio of 5 mol % (zinc atom mole ratio (Zn/substrate=Zn/S)), a transesterification reaction between methyl benzoate (1.0 mole equivalents) and benzyl alcohol (1.2 mole equivalents) was conducted. Consequently, benzyl benzoate was obtained in a yield of 92%.

Comparative Example 1

Transesterification Reaction Using Zinc Complex B

A reaction was conducted in the same manner as in Example 2, except that the catalyst was changed to the zinc complex B prepared in Example 1. Consequently, the transesterification reaction did not proceed.

Example 3

Transesterification Reaction Based on In-Situ Method

A reaction was conducted in the same manner as in Example 2, except that the same amount of $Zn_4(OCOCF_3)_6O$ and the ligand (A) (8 equivalents to $Zn_4(OCOCF_3)_6O$) were added as a catalyst instead of the zinc complex A. Consequently, benzyl benzoate was obtained in a yield of 91%.

Examples 4 to 10

Transesterification Reactions

Catalytic reactions were conducted as shown in the following formula in a chlorobenzene (PhCl) solvent by using $Zn_4(OCOCF_3)_6O$ (1 mole equivalent) and various ligands (8 mole equivalents, the ligand was 2 mole equivalents relative to 1 mole equivalent of zinc atoms) as catalysts, which were added to a transesterification reaction system between methyl benzoate and cyclohexanol (catalyst ratio: 1.25 mol %).

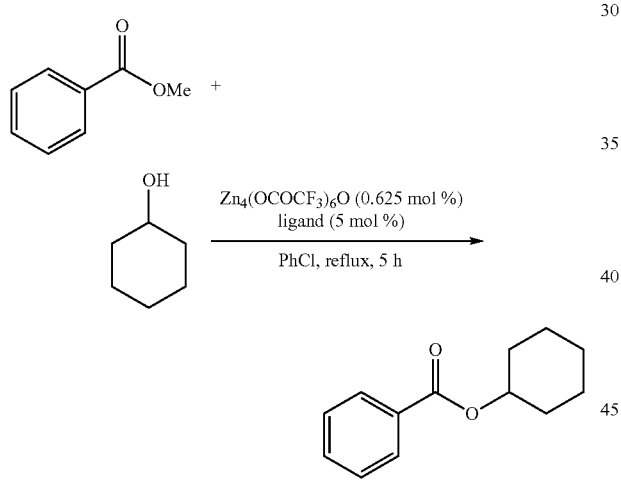

Table 2 below collectively shows the reaction results.

TABLE 2

| | Ligand | Yield (%) |
|---|---|---|
| Example 4 | ligand (A) | 89 |
| Example 5 | ligand (B) | 84 |
| Example 6 | ligand (C) | 80 |
| Example 7 | ligand (D) | 87 |
| Example 8 | ligand (E) | 52 |

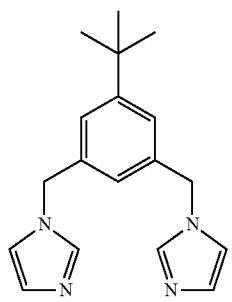
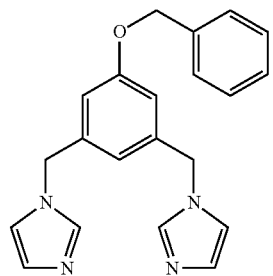
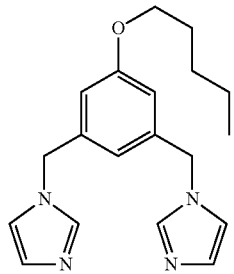
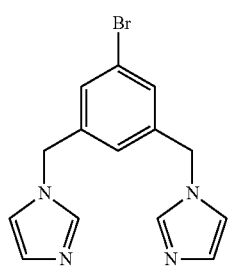

TABLE 2-continued

| | Ligand | Yield (%) |
|---|---|---|
| Example 9 | ligand (F) 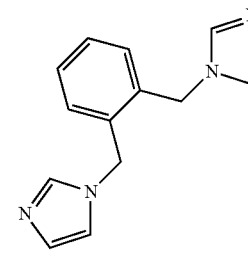 | 71 |
| Example 10 | ligand (G) 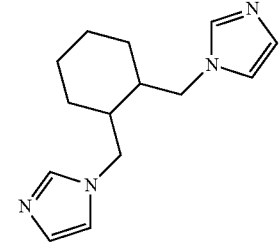 | 92 |
| No ligand | | 10 |
| | 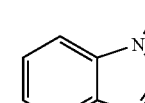 | 15 |

In addition, the yield was 10% in the case where no ligand was added, and the yield was 15% in the case where a different nitrogen-containing heterocyclic (N-methylbenzimidazole) compound was added as the ligand, revealing that the activity was lower in these cases than in the cases of the ligands used in the present invention.

Note that the ligands (C) to (G) were obtained by the methods shown in the following schemes.

Synthesis of Ligand (C)

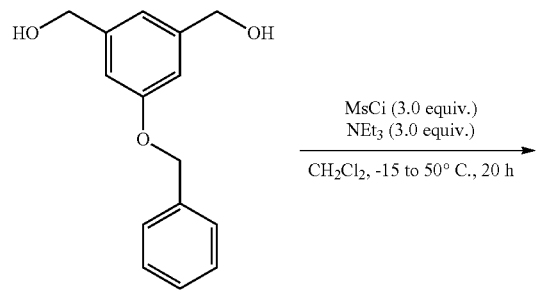

-continued

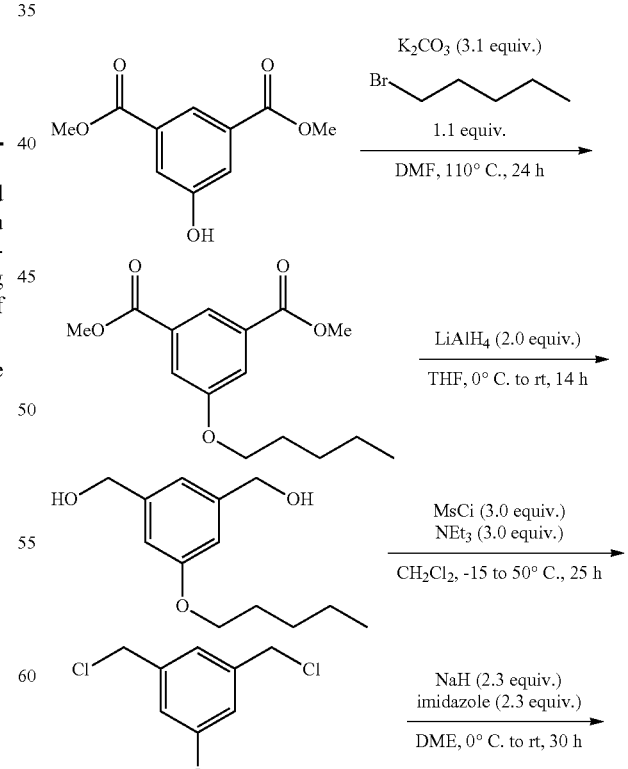

1H NMR (400 MHz, CDCl3) δ 7.51 (s, 2H, NCHN), 7.35 (m, 5H, Ar), 7.10 (s, 2H, CH2NCHCH), 6.86 (s, 2H, CH2NCHCH), 6.65 (s, 2H, Ar), 6.52 (s, 1H, CH2CCHCCH2), 5.04 (s, 4H, NCH2), 4.96 (s, 2H, OCH2)

Synthesis of Ligand (D)

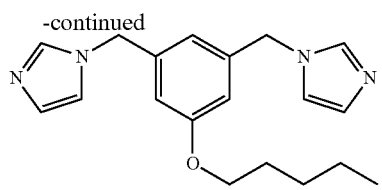

1H NMR (500 MHz, CDCl3) δ 7.52 (s, 2H, NCHN), 7.10 (s, 2H, CH2NCHCH), 6.88 (s, 2H, CH2NCHCH), 6.58 (s, 2H, Ar), 6.50 (s, 1H, Ar), 5.04 (s, 4H, NCH2), 3.84 (t, J=6.5 Hz, 2H, OCH2), 1.73 (tt, J=7.5, 6.5 Hz, 2H, OCH2CH2), 1.41-1.35 (m, 4H, CH2CH2CH3), 0.92 (t, J=7.0 Hz, 3H, CH3)

Synthesis of Ligand (E)

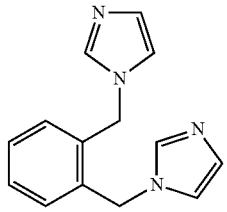

1H NMR (500 MHz, CDCl3) δ 7.44 (s, 2H, NCHN), 7.38 (dd, J=9.0, 2.5 Hz, 2H, Ar), 7.12 (s, 2H, CH2NCHCH), 7.09 (dd, J=9.0, 2.0 Hz, 2H, Ar), 6.79 (s, 2H, CH2NCHCH), 5.03 (s, 4H, NCH2)

Synthesis of Ligand (G)

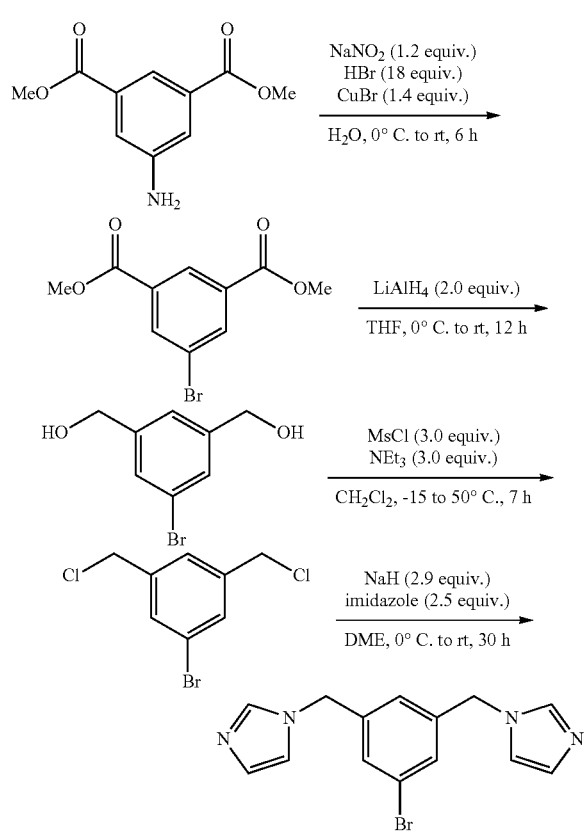

1H NMR (400 MHz, CDCl3) δ 7.45 (s, 2H, NCHN), 7.09 (s, 2H, CH2NCHCH), 6.86 (s, 2H, CH2NCHCH), 3.95 (d, J=7.6 Hz, 4H, NCH2), 2.11 (m, 2H, CH2CH2CH), 1.65 (m, 2H, CH2CH2CH), 1.47-1.33 (m, 6H, CH2CH2CH).

Examples 11 to 14

Transesterification Reactions

Reactions were conducted as shown in the following formula by changing the solvent to toluene and by using Zn4(OCOCF3)6O (1 mole equivalent) and various ligands (10 mole equivalents, each ligand was 2 mole equivalents relative to 1 mole equivalent of zinc atoms) as catalysts, which were added to a transesterification reaction system between methyl benzoate and benzyl alcohol (catalyst ratio: 1.25 mol %).

1H NMR (400 MHz, CDCl3) δ 7.53 (s, 2H, NCHN), 7.23 (s, 2H, CH2NCHCH), 7.12 (s, 2H, CH2NCHCH), 6.87 (s, 2H, Ar), 6.80 (s, 1H, Ar), 5.07 (s, 4H, CH2)

Synthesis of Ligand (F)

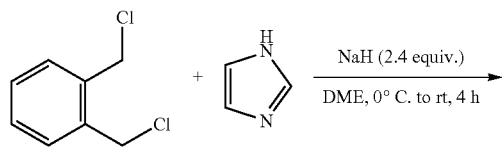

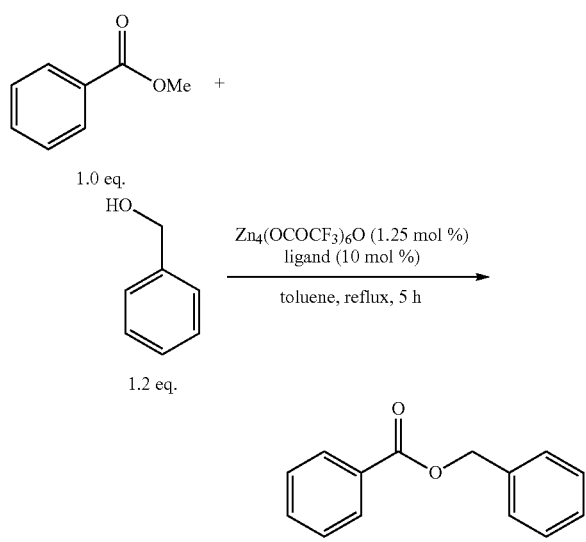

Table 3 below collectively shows the reaction results.

TABLE 3

| | Ligand | Yield (%) |
|---|---|---|
| Example 11 | ligand (A) | 91 |
| Example 12 | ligand (B) | 92 |
| Example 13 | ligand (C) | 97 |

TABLE 3-continued

| | Ligand | Yield (%) |
|---|---|---|
| Example 14 | ligand (D) | 97 |

When the ligand (D) of Example 14 was used as the catalyst, the system remained homogeneous one hour after the start of the reaction, but a solid was precipitated at the end of the reaction. The precipitated solid was recovered. The zinc complex C of the present invention serving as the catalyst was successfully recovered in a yield of 63%. A transesterification reaction was conducted by using the recovered zinc complex C in the same manner. The reaction proceeded in about the same yield (92%). Hence, it is conceivable that the catalyst of the present invention can provide good results, even when recycled.

Example 15

Transesterification Reactions (Recovery and Recycle Use of Catalyst)

In the following transesterification reaction, recycle use was examined in the case where the ligand (B) was used.

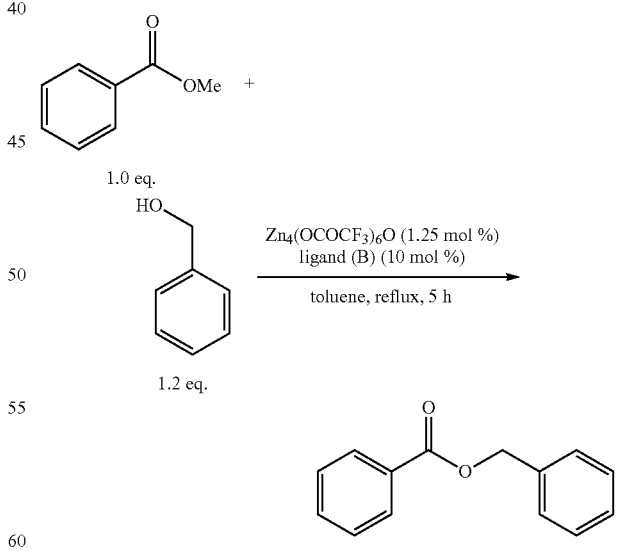

After the reactions (the yields of benzyl benzoate were all 90% or higher), each reaction liquid was allowed to cool to room temperature. Then, a solvent was added, followed by stirring. The solution part was removed, and then the residue was dried in a vacuum to recover the zinc complex. Table 4 shows the results.

| Example No. | Solvent | Recovery (%) |
|---|---|---|
| 15-1 | None | 63 |
| 15-2 | Hexane | 84 |
| 15-3 | Ethyl acetate | 78 |
| 15-4 | Diisopropyl ether | 69 |
| 15-5 | THF | 52 |
| 15-6 | Diethyl ether | 49 |
| 15-7 | Dichloromethane | <1 |

The conditions were further investigated. Consequently, it has been found that the complex can be recovered almost quantitatively by first removing the reaction solvent toluene by distillation, and then adding hexane. The catalyst was recovered by using this method, and the reaction was conducted again. The catalytic reaction was successfully carried out, without any decrease in the reaction yield from that of the previous reaction. In addition, after completion of the fifth reaction, the recovery was 91%.

Example 16

Transesterification Reaction

A reaction was conducted as shown in the following formula by adding 2 mole equivalents of the ligand (A) relative to 1 mole equivalent of zinc trifluoroacetate hydrate to the transesterification reaction system. With a zinc atom ratio of 3 mol % relative to methyl benzoate, reflux was conducted in chlorobenzene for 5 hours. Consequently, the conversion was 94%.

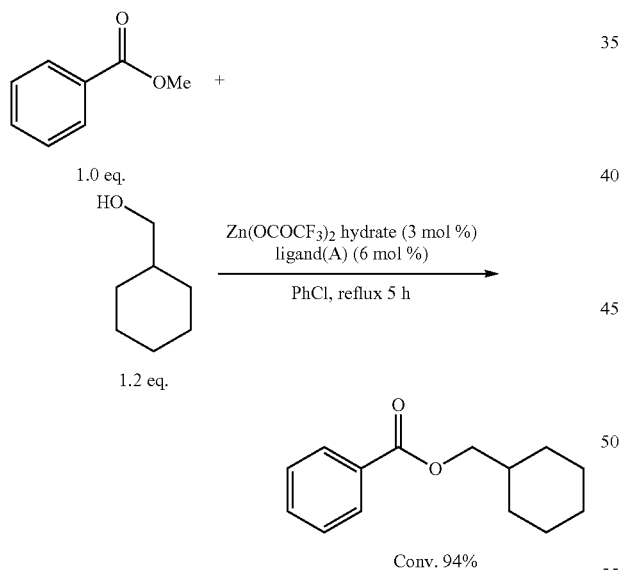

Example 17

Transesterification Reaction

A reaction was conducted in the same manner as in Example 16 described above. With a catalyst ratio of 2 mol % relative to methyl 4-cyanobenzoate, reflux was conducted in chlorobenzene for 5 hours. Consequently, the raw material methyl 4-cyanobenzoate disappeared, and the conversion was almost 100%.

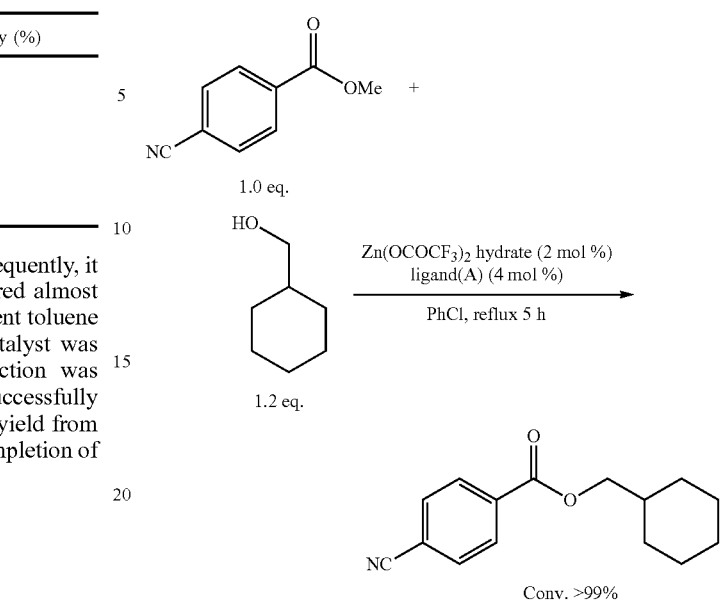

Example 18

Transesterification Reaction

A catalytic reaction was conducted as shown in the following formula by adding 2 mole equivalents of the ligand (A) relative to 1 mole equivalent of zinc trifluoroacetate hydrate to a transesterification reaction system. With a catalyst ratio of 3.3 mol % relative to methyl 4-nitrobenzoate, reflux was conducted in benzene chloride for 5 hours. The raw material methyl 4-nitrobenzoate disappeared, and the conversion was 99.9%.

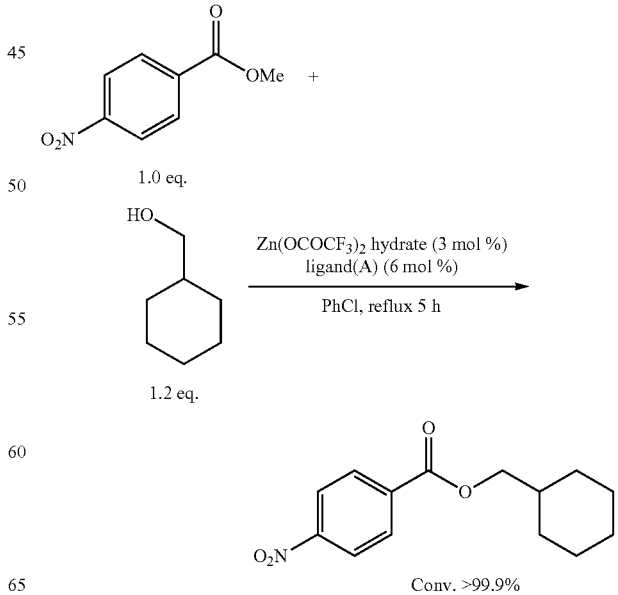

Example 19

Transesterification Reactions

Transesterification reactions between cyclohexylmethanol and methyl 4-nitrobenzoate or methyl 4-cyanobenzoate were conducted as shown in the following formula (solvent: chlorobenzene, 5 hours under reflux). With a catalyst ratio of 2.7 mol % relative to each substrate, the esterification reaction proceeded quantitatively.

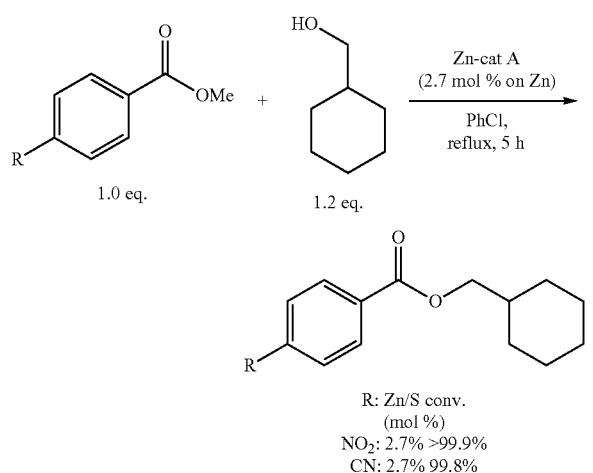

Example 20

Carbonate Formation Reaction

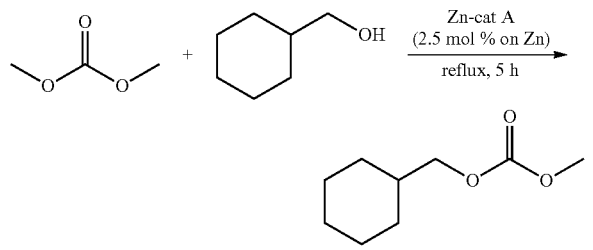

A carbonate formation reaction from cyclohexylmethanol was conducted by using the zinc complex A at a catalyst ratio of 2.5 mol % and using dimethyl carbonate as the solvent (5 hours under reflux). The raw material cyclohexylmethanol almost disappeared, and the carbonate formation reaction proceeded quantitatively.

As a recycle experiment, the catalyst was filtered, and then the above-described reaction was conducted again. As in the case of the first time, the raw material cyclohexylmethanol almost disappeared, and the transesterification reaction proceeded quantitatively. From this result, it has been found that the catalyst of the present invention can be used repeatedly.

Example 21

Carbonate Formation Reactions

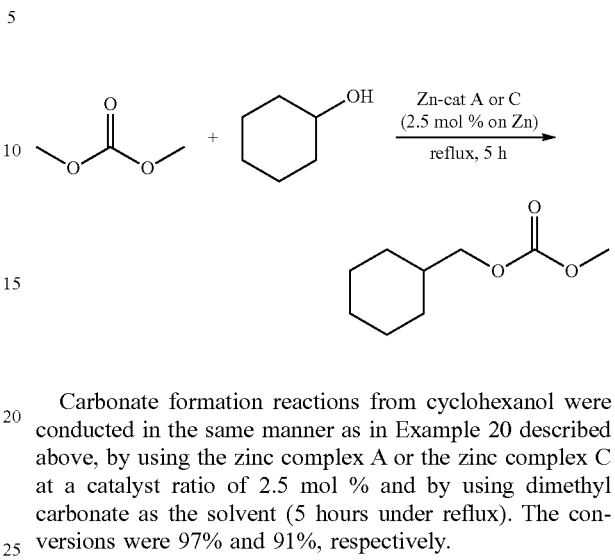

Carbonate formation reactions from cyclohexanol were conducted in the same manner as in Example 20 described above, by using the zinc complex A or the zinc complex C at a catalyst ratio of 2.5 mol % and by using dimethyl carbonate as the solvent (5 hours under reflux). The conversions were 97% and 91%, respectively.

Example 22

Acetylation Reaction

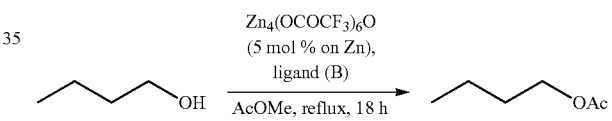

Acetylation of n-butanol with ethyl acetate was conducted by using the ligand (B) and $Zn_4(OCOCF_3)_6O$ as a catalyst. n-Butanol was refluxed in an ethyl acetate solvent for 18 hours. The target product was obtained in a yield of 99%.

Example 23

Hydroxy Group-Selective Acylation Reaction (Transesterification Reaction in the Presence of Alcohol and Amine

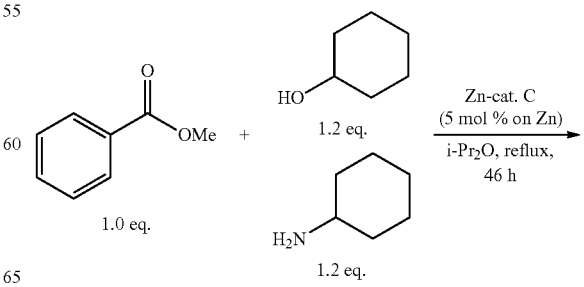

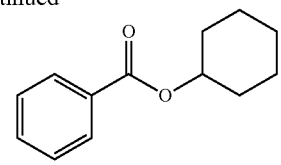

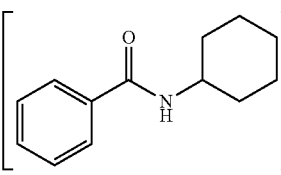

By using 5 mol % of the zinc complex C, a transesterification reaction of a mixture of cyclohexylamine and cyclohexanol with methyl benzoate was conducted under reflux for 46 hours by using diisopropyl ether (i-Pr$_2$O) as a solvent. Consequently, cyclohexyl benzoate was obtained in a yield of 67%, and cyclohexylbenzamide was not formed at all. It has been shown that the zinc complex can also be applied to an alcohol compound-selective acylation reaction in the presence of an amino compound.

Example 24

Hydroxy Group-Selective Acylation Reaction (Transesterification Reaction of Amino Alcohol)

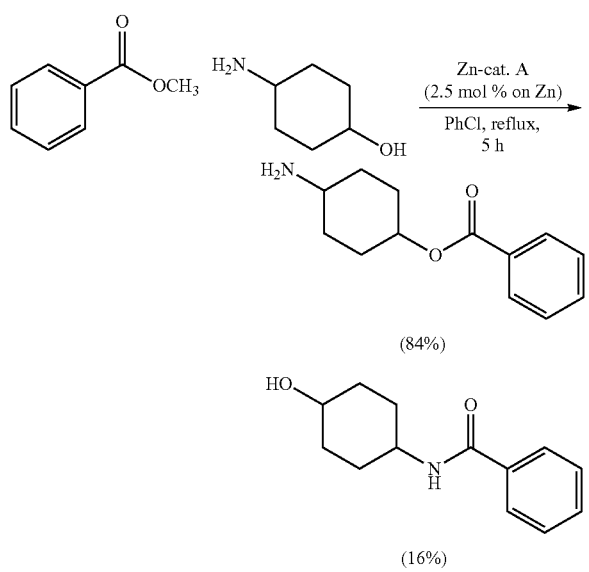

A transesterification reaction between methyl benzoate and trans-4-aminocyclohexanol was conducted by using 2.5 mol % of the zinc complex A (solvent: chlorobenzene (PhCl), 5 hours under reflux). The conversion was 75.9%, and the ratio (selectivity) of the compound produced by the reaction between the hydroxy group and methyl benzoate and the compound produced by the reaction between the amino group and methyl benzoate was 84:16. It has been shown that the complex can be applied to a hydroxy group-selective acylation reaction in the presence of an amino group.

Example 25

Hydroxy Group-Selective Carbonate Formation Reaction (Carbonate Formation in the Presence of Alcohol and Amine)

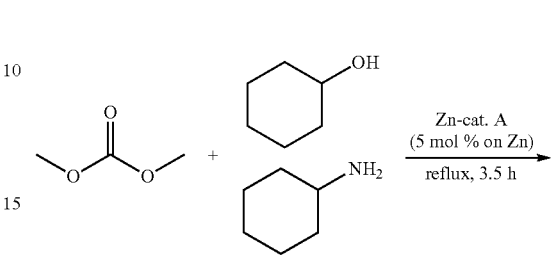

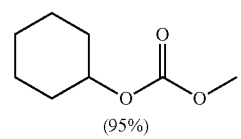

(95%)

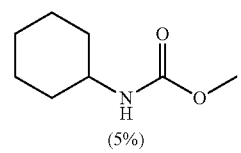

(5%)

For carbonate formation from cyclohexanol and cyclohexylamine using dimethyl carbonate as a solvent, reflux was conducted for 3.5 hours by using 5.0 mol % of the zinc complex A as a catalyst. The yield of the carbonate compound was 95%, and the yield of the carbamate compound was 5%. It has been shown that the complex can be applied also to an alcohol compound-selective carbonate formation reaction in the presence of an amino compound.

For the identification of the products, compounds were prepared by esterification and urethane formation of cyclohexanol and cyclohexylamine with methyl chloroformate separately, and the ratio of the products of this example was checked by a gas chromatography (GC) analysis.

Example 26

Hydroxy Group-Selective Carbonate Formation Reaction (Carbonate Formation from Amino Alcohol)

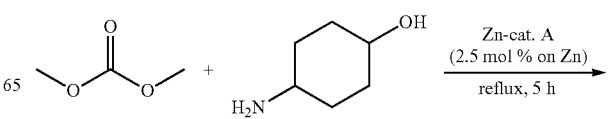

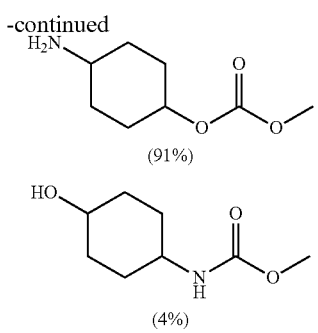

(91%)

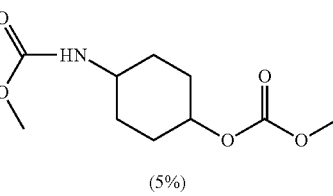

(4%)

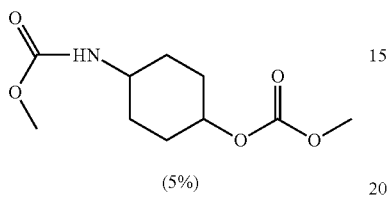

(5%)

A carbonate formation reaction between dimethyl carbonate and trans-4-aminocyclohexanol was conducted by using 2.5 mol % of the zinc complex A as a catalyst (5 hours under reflux). The conversion of trans-4-aminocyclohexanol was 86%, with an O-selectivity of 91%, an N-selectivity of 4%, and an O,N-selectivity of 5%. This shows that the zinc complex can be applied to a hydroxy group-selective carbonate formation reaction in the presence of an amino group. For the identification of the products, compounds were prepared by esterification and urethane formation of trans-4-aminocyclohexanol with methyl chloroformate, separately, and the ratio of the products of this example was checked by a gas chromatography (GC) analysis.

Example 27

Transesterification Reaction of Carbamate

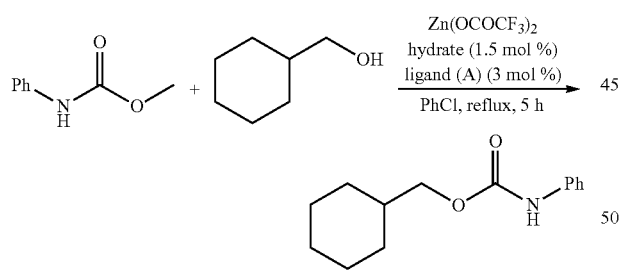

A transesterification reaction was conducted in a chlorobenzene solvent for 5 hours with a catalyst ratio of 1.5 mol % by using N-phenyl carbamate and cyclohexylmethanol and by adding 2 mole equivalents of the ligand (A) relative to 1 mole equivalent of zinc trifluoroacetate hydrate. Consequently, the conversion was 92%.

Example 28

Transesterification Reactions

Transesterification reactions were conducted by using methyl benzoate and L-menthol and using the zinc complex A or the zinc complex C as a catalyst (solvent: chlorobenzene (PhCl), 5 hours, reflux). Consequently, the product was obtained with conversions of 34% and 46%, respectively.

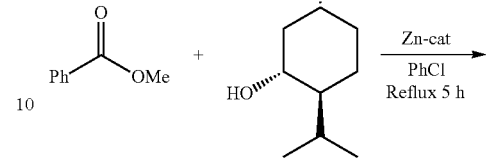

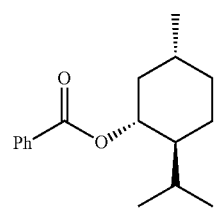

Zn-cat: Zn/S conv.
(mol %)
Zn-cat A: 2.3 34%
Zn-cat C: 2.8 46%

Example 29

Transesterification Reactions

Transesterification reactions were each conducted by using 1 equivalent of methyl benzoate and 1.2 equivalents of (+)-menthol, and adding $Zn_4(OCOCF_3)_6O$ and a ligand to prepare a catalyst (solvent: toluene, 5 hours, reflux). Table 5 shows the results of the transesterification reactions. When no ligand was added, the reaction did not proceed (Comparative Example 6).

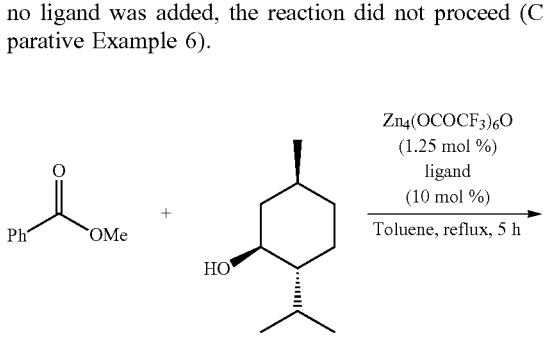

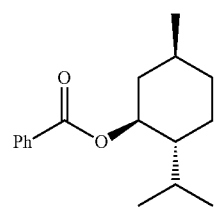

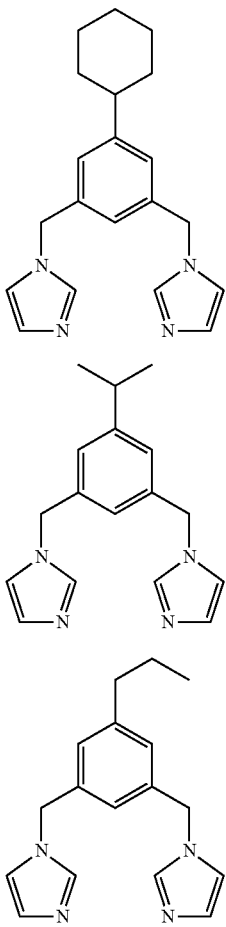

ligand (H)

ligand (I)

ligand (J)

TABLE 5

|  | Ligand | Yield |
| --- | --- | --- |
| Example 29-1 | D | 66% |
| Example 29-2 | H | 64% |
| Example 29-3 | I | 75% |
| Example 29-4 | J | 52% |
| Comp. Ex. 6 | None | N.D. |

The ligands (H), (I), and (J) were synthesized by using the ligand (E) as a raw material.

Ligand (H): $^1$H NMR (500 MHz, CDCl$_3$) δ 7.53 (s, 2H, NCHN), 7.10 (s, 2H, CH$_2$NCHCH), 6.92 (s, 2H, Ar), 6.88 (s, 2H, CH$_2$NCHCH), 6.72 (s, 1H, Ar), 5.07 (s, 4H, CH$_2$), 2.47-2.42 (m, 1H, CH), 1.83-1.71 (m, 6H, cyclohexyl), 1.40-1.20 (m, 4H, cyclohexyl); $^{13}$NMR (125 MHz, CDCl$_3$) δ150.1, 137.5, 137.1, 130.0, 125.6, 123.4, 119.2, 50.6, 44.3, 34.3, 26.7, 25.9.

Ligand (I): $^1$H NMR (500 MHz, CDCl$_3$) δ 7.53 (s, 2H, NCHN), 7.10 (s, 2H, CH$_2$NCHCH), 6.95 (s, 2H, Ar), 6.88 (s, 2H, CH$_2$NCHCH), 6.72 (s, 1H, Ar), 5.07 (s, 4H, CH$_2$), 2.85 (qq, J=7 Hz, 1H, CH), 1.19 (d, J=7 Hz, 6H, CH$_3$); $^{13}$C NMR (125 MHz, CDCl$_3$) δ 150.9, 137.4, 137.2, 130.0, 125.3, 123.5, 119.3, 50.6, 34.0, 23.8. Ligand (J): $^1$H NMR (500 MHz, CDCl$_3$) δ 7.53 (s, 2H, NCHN), 7.10 (s, 2H, CH$_2$NCHCH), 6.90 (s, 2H, Ar), 6.88 (s, 2H, CH$_2$NCHCH), 6.74 (s, 1H, Ar), 5.06 (s, 4H, CH$_2$), 2.52 (t, J=7.5 Hz, 2H, CH$_2$), 1.56 (tq, J=7.5, 7.0 Hz, 2H, CH$_2$CH$_3$), 0.90 (t, J=7.0 Hz, 3H); $^{13}$C NMR (125 MHz, CDCl$_3$) δ 144.7, 137.4, 137.1, 130.0, 127.2, 123.4, 119.3, 50.5, 37.7, 24.4, 13.7.

Example 30

Carbonate Formation Reactions

A carbonate formation reaction of each of L-menthol and D-menthol was conducted in a dimethyl carbonate solvent by using the zinc complex A at a catalyst ratio of 5.0 mol % (9 hours, reflux). Consequently, the raw materials menthols disappeared. The zinc catalyst was precipitated by adding hexane, and filtered. After evaporation of the solvent, each target product was octained quantitatively.

Each optical purity was checked by GC measurement. Consequently, the optical purity before the reaction was confirmed to be retained.

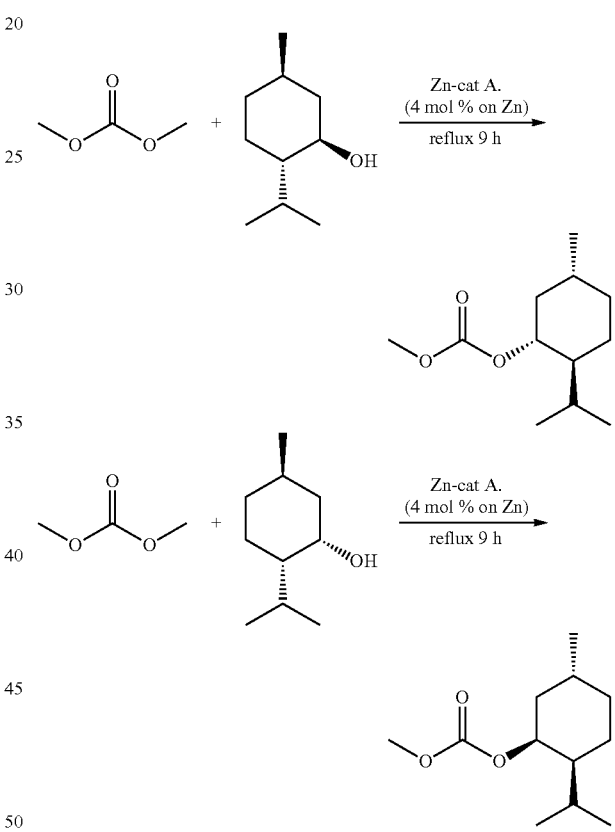

Example 31

Cyclic Carbonate Formation Reactions

In a dimethyl carbonate solvent, 1,2-butanediol was refluxed for 5 hours with the zinc catalyst A (a catalyst ratio of 2 mol %) being used. The conversion of 1,2-butanediol to 4-ethyl-1,3-dioxolan-2-one was 94%. In addition, another reaction was conducted by adding zinc trifluoroacetate hydrate (a catalyst ratio of 2 mol %) and the ligand (A) (a catalyst ratio of 4 mol %) in the same manner. Consequently, the raw material 1,2-butanediol disappeared in 9 hours, and the cyclic carbonate was successfully obtained as in the case where the zinc catalyst A was used.

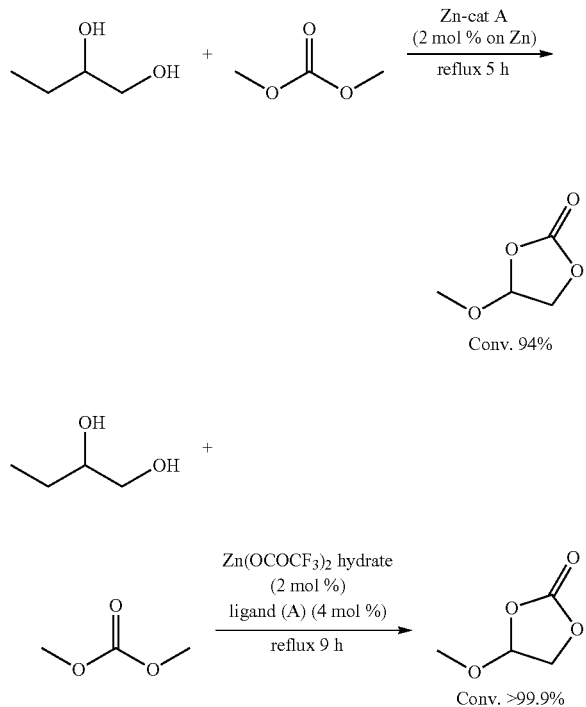

Conv. 94%

Conv. >99.9%

Comparative Example 7

Cyclic Carbonate Formation Reaction

A reaction was conducted by using Zn$_4$(OCOCF$_3$)$_6$O as a catalyst instead of the zinc catalyst A at a catalyst ratio of 2 mol % under reflux for 5 hours in the same manner as in Example 30. Consequently, the conversion of 1,2-butanediol was 53%, and the raw material 1,2-butanediol did not disappear even after reflux for 9 hours, and the reaction was not completed.

Example 32

Transesterification Reaction

A transesterification reaction between methyl acetoacetate and 1-adamantanol was conducted by using the zinc complex C (a catalyst ratio of 2.8 mol %) as a catalyst (solvent: chlorobenzene (PhCl), 5 hours under reflux). Consequently, the transesterification product was obtained with a conversion of 46%.

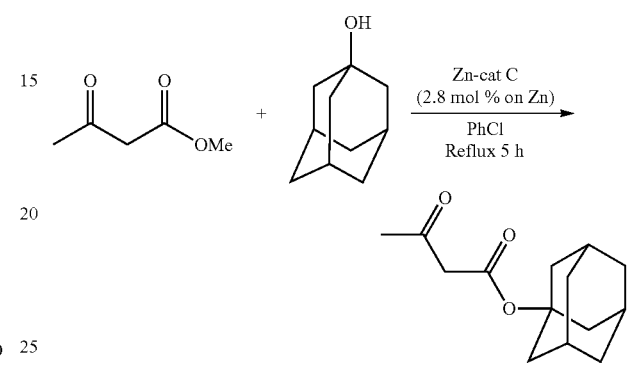

Examples 33 to 44

Transesterification Reactions

By the method of the present invention, transesterification reactions were conducted by using various ester compounds and alcohol compounds. The results are shown below.

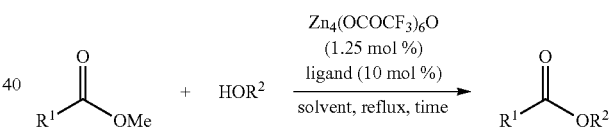

| Ex. | R$^1$ | R$^2$ | Ligand | Solvent | Time | Yield |
|---|---|---|---|---|---|---|
| 33 | CH2=CH— | cyclohexyl | D | i-Pr$_2$O | 18 hr | 78% |
| 34 | CH$_2$=C(Me)— | benzyl | D | iPr$_2$O | 18 hr | 76% |
| 35 | MeCH(Cl)— | benzyl | B | PhMe | 5 hr | 96% |
| 36 | H | benzyl | D | HCO$_2$Et | 24 hr | 82% |
| 37 | 2-tolyl | benzyl | D | PhMe | 5 hr | 85% |
| 38 | CbzHN–CH(iPr)– | n-butyl | D | i-Pr$_2$O | 18 hr | 93% |

-continued

| Ex. | R¹ | R² | Ligand | Solvent | Time | Yield |
|---|---|---|---|---|---|---|
| 39 | Ph | (cholesteryl group) | D | PhMe | 5 hr | 85% |
| 40 | Ph | (bornyl group) | D | PhMe | 18 hr | >99% |
| 41 | Ph | Me3Si—CH2CH2— | D | PhMe | 8 hr | 94% |
| 42 | Ph | (propargyl-NEt₂ group) | D | PhMe | 8 hr | 93% |
| 43 | PhCH₂CH₂— | 1-adamantyl | D | xylene | 72 hr | 92% |
| 44 | (ibuprofen-like group) | (2-pyridylmethyl group) | D | xylene | 38 hr | 82% |

Example 45

Deacylation Reaction

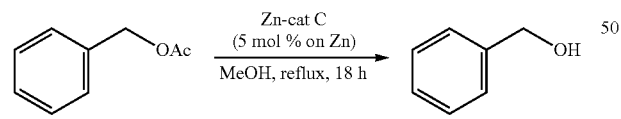

A deacetylation reaction of benzyl acetate was conducted in a methanol solvent by using the zinc complex C. Regarding the amount of the catalyst, 5 mol % of the catalyst was used in terms of the mole ratio of zinc atoms to benzyl acetate. The reaction yield was 93%.

The invention claimed is:

1. A zinc complex with an octahedral geometry, comprising a repeating unit represented by general formula (I):

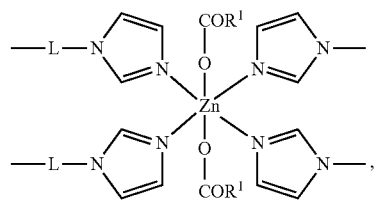

wherein L represents a linker moiety, and $R^1$ represents an alkyl group having 1 to 4 carbon atoms and optionally having a halogen atom(s).

2. A zinc complex obtained by reacting
a zinc carboxylate compound represented by general formula (III) or a zinc carboxylate compound represented by general formula (IV) with
a compound represented by general formula (V) in an amount of 2 mole equivalents to zinc atoms of the zinc carboxylate compound:

$$Zn(OCOR^{1a})_2 \cdot xH_2O \quad \text{(III)},$$

wherein $R^{1a}$ represents an alkyl group having 1 to 4 carbon atoms and optionally having a halogen atom(s), and x represents any number of 0 or greater;

$$Zn_4O(OCOR^{1b})_6(R^{1b}COOH)_n \quad \text{(IV)},$$

wherein $R^{1b}$ represents an alkyl group having 1 to 4 carbon atoms and optionally having a halogen atom(s), and n represents 0 to 1; and

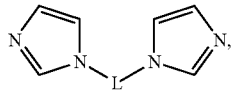

(V)

wherein L represents a linker moiety.

3. The zinc complex according to claim 2, wherein the linker L is represented by general formula (II):

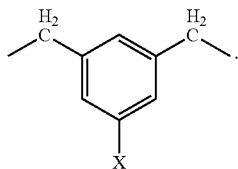

(II)

wherein X represents a hydrogen atom, an optionally substituted alkyl group having 1 to 10 carbon atoms, an optionally substituted alkoxy group having 1 to 10 carbon atoms, an optionally substituted aryl group, an optionally substituted allyl group, or a substituted amino group.

4. A catalyst comprising the zinc complex according to claim 1.

5. A method for acylating a hydroxy group, comprising reacting a carboxylic acid or an ester thereof in the presence of the catalyst according to claim 4.

6. A method for converting a hydroxy group to a carbonate, comprising
reacting a carbonate ester in the presence of the catalyst according to claim 4.

7. A method for deacylating a carboxylate ester, comprising
deacylating the carboxylate ester in the presence of the catalyst according to claim 4.

8. A method for acylating a hydroxy group with a carboxylic acid or an ester thereof, comprising
forming a catalyst by adding a zinc carboxylate compound represented by general formula (III) or a zinc carboxylate compound represented by general formula (IV) together with a compound represented by general formula (V) to an acylation reaction system:

$$Zn(OCOR^{1a})_2 \cdot xH_2O \quad (III),$$

wherein $R^{1a}$ represents an alkyl group having 1 to 4 carbon atoms and optionally having a halogen atom(s), and x represents any number of 0 or greater;

$$Zn_4O(OCOR^{1b})_6(R^{1b}COOH)_n \quad (IV),$$

wherein $R^{1b}$ represents an alkyl group having 1 to 4 carbon atoms and optionally having a halogen atom(s), and n represents 0 to 1; and

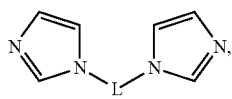

(V)

wherein L represents a linker moiety.

9. A method for converting a hydroxy group to a carbonate with a carbonate ester, comprising
forming a catalyst by adding a zinc carboxylate compound represented by general formula (III) or a zinc carboxylate compound represented by general formula (IV) together with a compound represented by general formula (V) to a carbonate formation reaction system:

$$Zn(OCOR^{1a})_2 \cdot xH_2O \quad (III),$$

wherein $R^{1a}$ represents an alkyl group having 1 to 4 carbon atoms and optionally having a halogen atom(s), and x represents any number of 0 or greater;

$$Zn_4O(OCOR^{1b})_6(R^{1b}COOH)_n \quad (IV),$$

wherein $R^{1b}$ represents an alkyl group having 1 to 4 carbon atoms and optionally having a halogen atom(s), and n represents 0 to 1; and

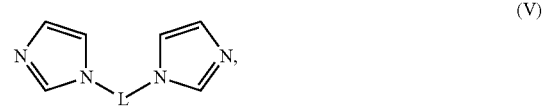

(V)

wherein L represents a linker moiety.

10. A method for deacylating a carboxylate ester, comprising
forming a catalyst by adding a zinc carboxylate compound represented by general formula (III) or a zinc carboxylate compound represented by general formula (IV) together with a compound represented by general formula (V) to a deacylation reaction system:

$$Zn(OCOR^{1a})_2 \cdot xH_2O \quad (III),$$

wherein $R^{1a}$ represents an alkyl group having 1 to 4 carbon atoms and optionally having a halogen atom(s), and x represents any number of 0 or greater;

$$Zn_4O(OCOR^{1b})_6(R^{1b}COOH)_n \quad (IV),$$

wherein $R^{1b}$ represents an alkyl group having 1 to 4 carbon atoms and optionally having a halogen atom(s), and n represents 0 to 1; and

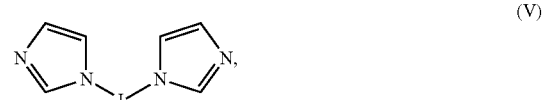

(V)

wherein L represents a linker moiety.

11. A method for producing a zinc complex represented by general formula (I), comprising
reacting a zinc carboxylate compound represented by general formula (III) or a zinc carboxylate compound represented by general formula (IV) with
a compound represented by general formula (V) in an amount of 2 mole equivalents to zinc atoms of the zinc carboxylate compound:

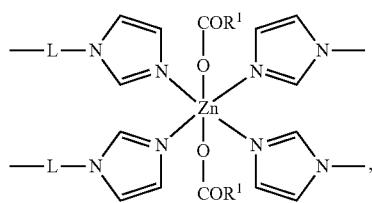 (I)

wherein L represents a linker moiety, and $R^1$ represents an alkyl group having 1 to 4 carbon atoms and optionally having a halogen atom(s);

$$Zn(OCOR^{1a})_2 \cdot xH_2O \quad (III),$$

wherein $R^{1a}$ represents an alkyl group having 1 to 4 carbon atoms and optionally having a halogen atom(s), and x represents any number of 0 or greater;

$$Zn_4O(OCOR^{1b})_6(R^{1b}COOH)_n \quad (IV),$$

wherein $R^{1b}$ represents an alkyl group having 1 to 4 carbon atoms and optionally having a halogen atom(s), and n represents 0 to 1; and

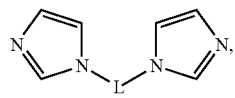 (V)

wherein L represents a linker moiety.

12. The zinc complex according to claim 2, wherein the linker L is represented by general formula (II):

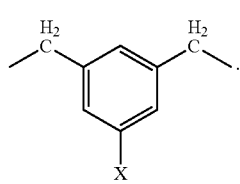 (II)

wherein X represents a hydrogen atom, an optionally substituted alkyl group having 1 to 10 carbon atoms, an optionally substituted alkoxy group having 1 to 10 carbon atoms, an optionally substituted aryl group, an optionally substituted allyl group, or a substituted amino group.

13. A catalyst comprising the zinc complex according to claim 2.

14. A method for acylating a hydroxy group, comprising reacting a carboxylic acid or an ester thereof in the presence of the catalyst according to claim 13.

15. A method for converting a hydroxy group to a carbonate, comprising
reacting a carbonate ester in the presence of the catalyst according to claim 13.

16. A method for deacylating a carboxylate ester, comprising
deacylating the carboxylate ester in the presence of the catalyst according to claim 13.

* * * * *